United States Patent [19]
Pawelka et al.

[11] Patent Number: 5,584,815
[45] Date of Patent: Dec. 17, 1996

[54] MULTI-CARTRIDGE MEDICATION INJECTION DEVICE

[75] Inventors: Gerhard E. F. Pawelka, Lexington, Mass.; Christopher J. Stringer, San Francisco, Calif.; Matthew Marsh, San Francisco, Calif.; David L. Karshmer, San Francisco, Calif.; Christopher O. Lada, Palo Alto, Calif.; Stephen J. Schoenberg, Redwood City, Calif.

[73] Assignee: Eli Lilly and Company, Indianapolis, Ind.

[21] Appl. No.: 424,660

[22] Filed: Apr. 19, 1995

Related U.S. Application Data

[63] Continuation-in-part of Ser. No. 333,207, Nov. 2, 1994, Pat. No. 5,478,323, and a continuation-in-part of Ser. No. 335,674, Nov. 8, 1994, abandoned, which is a continuation of Ser. No. 41,758, Apr. 2, 1993, abandoned.

[51] Int. Cl.$^6$ ..................................................... A61M 5/00
[52] U.S. Cl. ............................ 604/191; 604/83; 604/186; 604/135; 604/211; 604/51
[58] Field of Search ...................... 604/191, 90, 82–83, 604/211, 232, 237, 205, 186, 240, 207–209, 135–137

[56] References Cited

U.S. PATENT DOCUMENTS

| | | |
|---|---|---|
| 1,093,471 | 4/1914 | Porter . |
| 2,112,160 | 3/1938 | Johnson . |
| 2,221,739 | 11/1940 | Reiter . |
| 2,632,445 | 3/1953 | Kas, Sr. . |
| 3,002,517 | 10/1961 | Pitton . |
| 3,110,310 | 11/1963 | Cislak . |
| 3,232,117 | 2/1966 | Gilmont . |
| 3,481,510 | 12/1969 | Allen, Jr. . |
| 3,517,668 | 6/1970 | Brickson . |
| 3,583,399 | 6/1971 | Ritsky . |
| 3,613,952 | 10/1971 | Gilmont . |
| 3,815,785 | 6/1974 | Gilmont . |
| 4,018,223 | 4/1977 | Ethington . |
| 4,040,420 | 8/1977 | Speer . |
| 4,044,757 | 8/1977 | McWhorter . |
| 4,096,751 | 6/1978 | Withers . |
| 4,099,548 | 7/1978 | Sturm et al. . |

(List continued on next page.)

FOREIGN PATENT DOCUMENTS

| | | |
|---|---|---|
| 2108691 | 8/1993 | Canada . |
| 2074565 | 1/1995 | Canada . |
| 0058536 | 2/1982 | European Pat. Off. . |
| 0498737A1 | 2/1992 | European Pat. Off. . |
| 0627229A1 | 5/1994 | European Pat. Off. . |
| 1070784 | 5/1957 | Germany . |
| 3903315A1 | 8/1989 | Germany . |
| 1198214 | 7/1970 | United Kingdom . |
| 2172937 | 10/1986 | United Kingdom . |
| WO92/10425 | 6/1992 | WIPO . |
| WO92/18179 | 10/1992 | WIPO . |
| WO93/10838 | 6/1993 | WIPO . |
| WO94/11039 | 5/1994 | WIPO . |
| WO94/15120 | 7/1994 | WIPO . |

*Primary Examiner*—Randall L. Green
*Assistant Examiner*—Perry E. Van Over
*Attorney, Agent, or Firm*—Baker & Daniels

[57] ABSTRACT

A multi-cartridge dispenser for delivering two liquid medications through a single needle. The dispenser includes independent dual channel metering mechanism, dual channel drive mechanisms, and dual channel lock and pullback mechanisms. The wing must be in its "up" position for metering to take place. The wing reciprocatingly moves a driver between a pre-injection position and a post-injection position to reciprocatingly advance the leadscrews upon an injection stroke. The dosage indicator automatically rotates to its initial zero position upon the injection stroke. The lock and pullback mechanism automatically prevents rotation of the leadscrew upon metering and injection. It also locks out the cartridge retainers so that the retainers can be removed from the housing only while the wing is in its "down" position. The pullback sleeve unloads a pullback key during a cartridge change in order to enable the leadscrew to be spun freely back to its home position.

64 Claims, 13 Drawing Sheets

U.S. PATENT DOCUMENTS

| | | |
|---|---|---|
| 4,275,759 | 6/1981 | Silver . |
| 4,333,458 | 6/1982 | Margulies . |
| 4,359,049 | 11/1982 | Redl et al. . |
| 4,367,739 | 1/1983 | LeVeen et al. . |
| 4,381,778 | 5/1983 | Kozam et al. . |
| 4,395,921 | 8/1983 | Oppenlander . |
| 4,413,760 | 11/1983 | Paton . |
| 4,425,121 | 1/1984 | Young et al. . |
| 4,444,560 | 4/1984 | Jacklich . |
| 4,475,905 | 10/1984 | Himmelstrup . |
| 4,498,904 | 2/1985 | Turner et al. . |
| 4,581,022 | 4/1986 | Leonard et al. . |
| 4,592,745 | 6/1986 | Rex et al. . |
| 4,609,371 | 9/1986 | Pizzino . |
| 4,610,666 | 9/1986 | Pizzino . |
| 4,631,055 | 12/1986 | Redl et al. . |
| 4,643,723 | 2/1987 | Smit . |
| 4,659,327 | 4/1987 | Bennett et al. . |
| 4,664,128 | 5/1987 | Lee . |
| 4,673,395 | 6/1987 | Phillips . |
| 4,689,042 | 8/1987 | Sarnoff et al. . |
| 4,710,172 | 12/1987 | Jacklich et al. . |
| 4,710,178 | 12/1987 | Leonard et al. . |
| 4,755,169 | 7/1988 | Sarnoff et al. . |
| 4,820,287 | 4/1989 | Leonard . |
| 4,874,368 | 10/1989 | Miller et al. . |
| 4,883,472 | 11/1989 | Michel . |
| 4,968,299 | 11/1990 | Ahlstrand . |
| 4,973,318 | 11/1990 | Holm et al. . |
| 4,978,336 | 12/1990 | Capozzi . |
| 5,092,842 | 3/1992 | Bechtold et al. . |
| 5,104,375 | 4/1992 | Wolf et al. . |
| 5,104,380 | 4/1992 | Holman et al. . |
| 5,112,317 | 5/1992 | Michel . |
| 5,114,406 | 5/1992 | Gabriel et al. . |
| 5,116,315 | 5/1992 | Capozzi et al. . |
| 5,135,507 | 8/1992 | Haber et al. . |
| 5,147,323 | 9/1992 | Haber et al. . |
| 5,226,895 | 7/1993 | Harris . |
| 5,240,146 | 8/1993 | Smedley et al. . |
| 5,253,785 | 10/1993 | Haber et al. . |
| 5,271,527 | 12/1993 | Haber et al. . |
| 5,279,585 | 1/1994 | Balkwill . |
| 5,279,586 | 1/1994 | Balkwill . |
| 5,281,198 | 1/1994 | Haber et al. . |
| 5,295,976 | 3/1994 | Harris . |
| 5,304,152 | 4/1994 | Sams . |
| 5,314,412 | 5/1994 | Rex . |
| 5,378,233 | 1/1995 | Haber et al. . |
| 5,383,865 | 1/1995 | Michel . |

MULTI-CARTRIDGE MEDICATION INJECTION DEVICE

CROSS-REFERENCE TO RELATED APPLICATIONS

This is a continuation-in-part of U.S. application Ser. No. 08/333,207, filed Nov. 2, 1994, now U.S. Pat. No. 5,478,323, entitled MANIFOLD FOR INJECTION APPARATUS, and a continuation-in-part of U.S. patent application Ser. No. 08/335,674, now abandoned, filed Nov. 8, 1994, entitled MANIFOLD MEDICATION INJECTION APPARATUS AND METHOD, which is a continuation of application Ser. No. 08/041,758, Apr. 2, 1993, now abandoned.

BACKGROUND OF THE INVENTION

The present invention relates generally to devices for injecting two or more medications simultaneously and, more particularly, to a medication injection device having improved dose setting and injection capabilities.

It is medically desirable in the treatment of certain conditions of the human body to administer two or more types of medication simultaneously. The treatment of diabetes is one such example. Under certain conditions, it is desirable to simultaneously deliver two types of insulin: fast acting insulin and an intermediate acting insulin, such as isophene insulin, which takes effect more slowly but for a longer period of time. Also, a longer acting type of insulin called ultralente is available. In order to most accurately simulate the natural glucose curve of the body, the insulin user injects different ratios or combinations of these insulins several times daily.

In order to achieve such injection capability, there have been developed injection devices in which separate cartridges of a desired medication are housed. It is desirable that both medications be delivered to a patient through a single needle instead of two or more needles. Therefore, such injection devices have a manifold assembly that enables the medications to be mixed together prior to injection.

One such type of injection device is proposed in U.S. Pat. No. 5,253,785. This patent asserts a dispenser for injecting variable mixed proportions of NPH and regular human insulin. The dosages of each medication are set prior to delivery. Dosing is achieved by rotating a dose knob to translate a dosage adjuster to a retracted position. The second dosage knob is adjusted in a similar manner. The dosage adjusters are coupled to a sliding body. After the appropriate dosages are set, the sliding body is forced forwardly, which causes the drive stems to translate forwardly. Since the drive stems are connected to pistons within each medication cartridge, movement of the drive stems drives the pistons forward to expel liquid from the cartridges. The forward stroke of the sliding body is limited by the distance set by the dosage adjusters.

Another type of dual medication injection device is proposed in PCT International Application No. PCT/US93/11044. In this device, dosage knobs are rotated to translate the dosage adjusters to their retracted positions. Movement of the dosage adjusters compresses springs, which engage flanges on the adjusters. This compression preloads the drive stems so that moving the needle assembly from the predelivery position to the delivery position causes the dosages of pharmaceutical to be automatically driven from the pharmaceutical chambers, past the check valves and through the doubled ended needle cannula.

SUMMARY OF THE INVENTION

The present invention provides in one embodiment thereof a hand-held liquid medication delivery device capable of simultaneously delivering at least two medication products. The medication products are housed in variable volume containers or cartridges within the mechanism housing of the device. Each cartridge contains a liquid medication between a piston and an exit end. The medication delivery device includes independent bidirectional dosage metering mechanisms for permitting a variable dosage amount of each liquid medication to be set prior to delivery. A delivery mechanism is provided for simultaneously axially advancing piston-engaging stems to engage and axially advance the pistons in the cartridges to effect delivery of the medications into a manifold at the distal end of the device. The medications are mixed within a valved mixing chamber in the manifold and the mixed product is delivered through a single delivery needle extending from the manifold. A lock and pullback mechanism incorporated into the delivery device automatically prevents the cartridges from being removed from the housing while the injection actuator is in a metering or pre-injection position. The cartridges are replaced after the contents thereof have been exhausted.

In one embodiment, the present invention provides a medication delivery device having a dosage metering mechanism for setting a dosage of liquid medication to be delivered prior to injection. The dosage metering mechanism includes a knob and indicator dial which function as a single component that is rotatable with respect to the mechanism housing. The mechanism includes an indicator bearing that is locked to the housing. A torsion spring is loaded between the knob and the bearing. The knob/indicator dial is coupled to a movable element on the drive mechanism. Upon rotation of the knob to set a dosage of liquid medication to be delivered the spring is tensed, and a dosage is indicated by a numeral on the indicator dial appearing in a window in the housing. Upon actuating the delivery mechanism, the movable element is moved out of engagement with knob/indicator dial, thereby enabling the spring to automatically rotate the indicator dial back to a zero dose position.

In one embodiment of the present invention, a multi-component medication delivery device is provided having a drive mechanism for simultaneously delivering a set dosage of each injectable product. An elongated tubular element or nut and a drive stem is associated with each liquid medication to be delivered. A driver or carrier is secured to each nut. Each driver is pivotally secured to a hand-operated actuator via side plates. Upon a single stroke of the actuator from its pre-injection position to its post-injection position, each of the drivers are simultaneously driven forwardly carrying the nut and drive stem therealong. The drive stems engage and axially advance their respective pistons to force the respective set dosages of liquid medications into the manifold and out through the delivery needle. Upon movement of the actuator back to its pre-injection position, the drive stems are moved off of their respective pistons back into a retracted position within the housing.

The present invention further provides in one form thereof a liquid medication delivery device having a lock and pullback mechanism which prevents the drive stems or leadscrews from rotating during metering and injection. This mechanism also prevents the cartridges from being changed during metering and injection. The lock and pullback mechanism includes a pullback key having an opening matching the shape of the leadscrew and being rotatable with the leadscrew, a pullback sleeve which is engageable and disengageable with the pullback key, a lock key which is rotatable with respect to the pullback sleeve, and a spring-loaded snap lock. While the actuator is in its pre-injection or dose-setting position, the lock key is locked in a first rotational position. In this first rotational position, the lock key forces the pullback key and the pullback sleeve into engagement with one another. Since the pullback sleeve is locked against rotation with respect to the housing, the pullback key and leadscrew are prevented from being able to rotate with respect to the housing. Upon injection, the drive nut engages and slightly axially advances the pullback sleeve and the lock key with respect to the housing. This moves the fingers of the lock key out of radial engagement with interfering ribs on the inner surface of the housing to enable the lock key to be rotated between a first rotational position and a second rotational position. Upon rotation of the lock key to its second position, the lock key moves slightly axially with respect to the pullback sleeve. This permits the pullback key to become disengaged from the pullback sleeve to allow the pullback key and leadscrew to rotate with respect to the pullback sleeve.

A cartridge retainer containing a cartridge of liquid medication is received within the nosepiece of the housing and rotatable within the nosepiece between a locked rotational position, in which the retainer cannot be removed from the nosepiece, and an unlocked rotational position in which the retainer can be removed from the nosepiece. The retainer includes tabs that are keyed for rotation with the lock key. Thus, the retainer is locked against rotation in its locked position while the actuator is in its pre-injection position, and the retainer is rotatable with the lock key to its unlocked position while the actuator is in its post-injection position, thereby enabling the retainer and spent cartridge to be removed and replaced with a new variable volume cartridge. Upon securing the new cartridge onto the housing, the piston of the new cartridge engages and axially spins the leadscrew back to its home position. This is possible since the leadscrew can rotate with respect to the housing while the actuator is in its post-injection position.

In one embodiment of the present invention, a multi-component medication delivery device is provided having a drive mechanism for simultaneously delivering a selectively set dosage of each injectable product. The device comprises a mechanism housing and a plurality of variable volume cartridges containing the medication and disposed within the housing, wherein each cartridge defines an axis of delivery of the medication from its respective cartridge. An elongated tubular element or nut and a drive stem is associated with each cartridge. A driver or carrier is secured to each nut. Each driver is pivotally secured to a hand-operated actuator via side plates. During metering, the actuator is in its "up" position, and each leadscrew is advanced a desired distance to set a desired dosage of product to be delivered. After the desired dosages have been set, the actuator is moved in a direction transverse to the axes of delivery, toward the housing, and into its "down" position. Upon this single stroke, each of the drivers are simultaneously driven forwardly carrying the nut and drive stem therealong. The drive stems engage and axially advance their respective pistons to force the respective set dosages of liquid medications into the manifold and out through the delivery needle. As the actuator moves into its "down" position, a groove in the actuator receives a tab on the housing resulting in an audible "click" to indicate an end of dose to the user.

An advantage of the present invention is that the device enables a user to independently set each dosage of product to be delivered.

Another advantage of the present invention is that the device enables bidirectional metering of each dosage to be set.

Another advantage of the present invention is that the device is capable of indicating and locking out metering of an insufficient remaining volume of liquid medication in a cartridge.

Another advantage of the present invention is that the device provides a tactile, visual, and auditory feedback during metering.

Another advantage of the present invention is that the device provides both a visual and auditory indication of an end of dose.

Another advantage of the present invention is that the metering mechanism automatically resets upon injection, thereby eliminating the need to manually reset the indicator dial back to zero prior to subsequent metering.

Another advantage of the present invention is that metering can be achieved only while the actuator is in the "wing up" or pre-injection position, thereby ensuring proper metering.

Another advantage of the present invention is that the device automatically prevents a user from attempting to change cartridges while the device is in its metering or pre-injection position, thereby maintaining dosing accuracy.

Another advantage of the present invention is that the leadscrew is automatically unlocked upon a cartridge change, thereby enabling the leadscrew to spin freely back to its home position upon inserting a new cartridge into the housing.

Other advantages will become apparent in the detailed description of a preferred embodiment of the invention.

DESCRIPTION OF A PREFERRED EMBODIMENT

Figure 1:
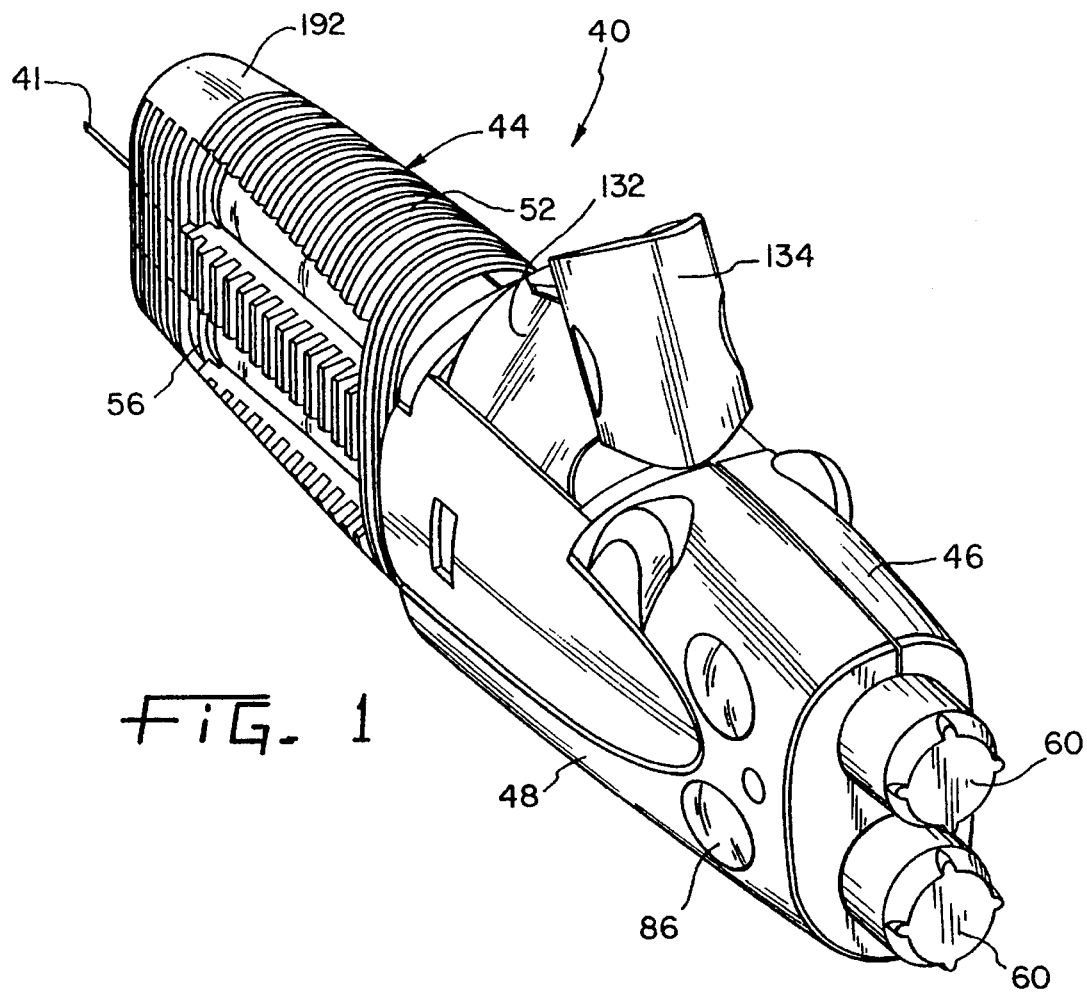
FIG. 1 is a perspective view of an embodiment of a medication dispensing device in accordance with the present invention, wherein the wing is shown in its "up" position.
Figure 2:
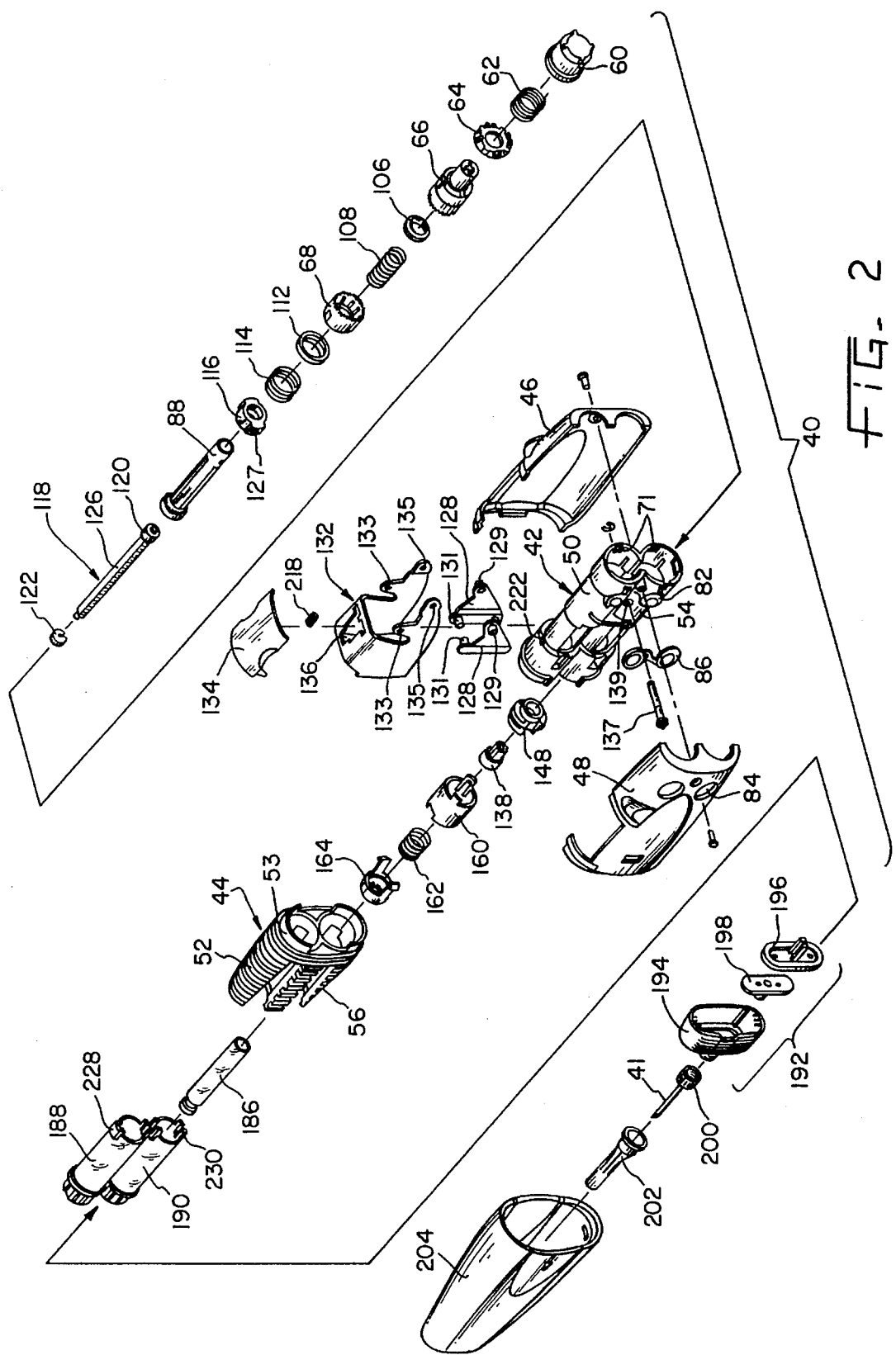
FIG. 2 is an exploded view of the device of FIG. 1.

In an embodiment of the invention as shown in the drawings, and in particular by referring to FIGS. 1 and 2, there is shown a medication dispensing device 40 for dispensing two different liquid medications as a mixed product through a single needle 41. The injection device includes a mechanism housing 42 (FIG. 2) and a nosepiece 44. Mechanism housing 42 is contained in housing covers 46 and 48. Both mechanism housing 42 and nosepiece 44 are clear plastic materials made of ABS resins or polycarbonates. In one embodiment, mechanism housing 42 and nosepiece 44 are ultrasonically welded to one another. In one method, the mechanism housing is placed in a nest supported by the back side of the ribs of the nosepiece, and a far field weld is performed with a horn on the top of the nosepiece. In another method, the mechanism housing and nosepiece are spring loaded together, and weld energy is injected orthogonally to the pressure direction at the semicircular ribs of the nosepiece.

Mechanism housing 42 comprises two parallel tubular components 50 and 54 for housing the individual components of device 40. Nosepiece 44 is also in the form of two parallel tubular components 52 and 56. Together, tubular components 50 and 52 form a first tubular member and tubular components 54 and 56 form a second tubular member. Although two parallel tubular members are shown in the drawings, it is possible that additional tubular members may be provided to meter and deliver three or more liquid medications from a single delivery device. Additional features of mechanism housing 42 and nosepiece 44 shall be described infra.

Figure 3:
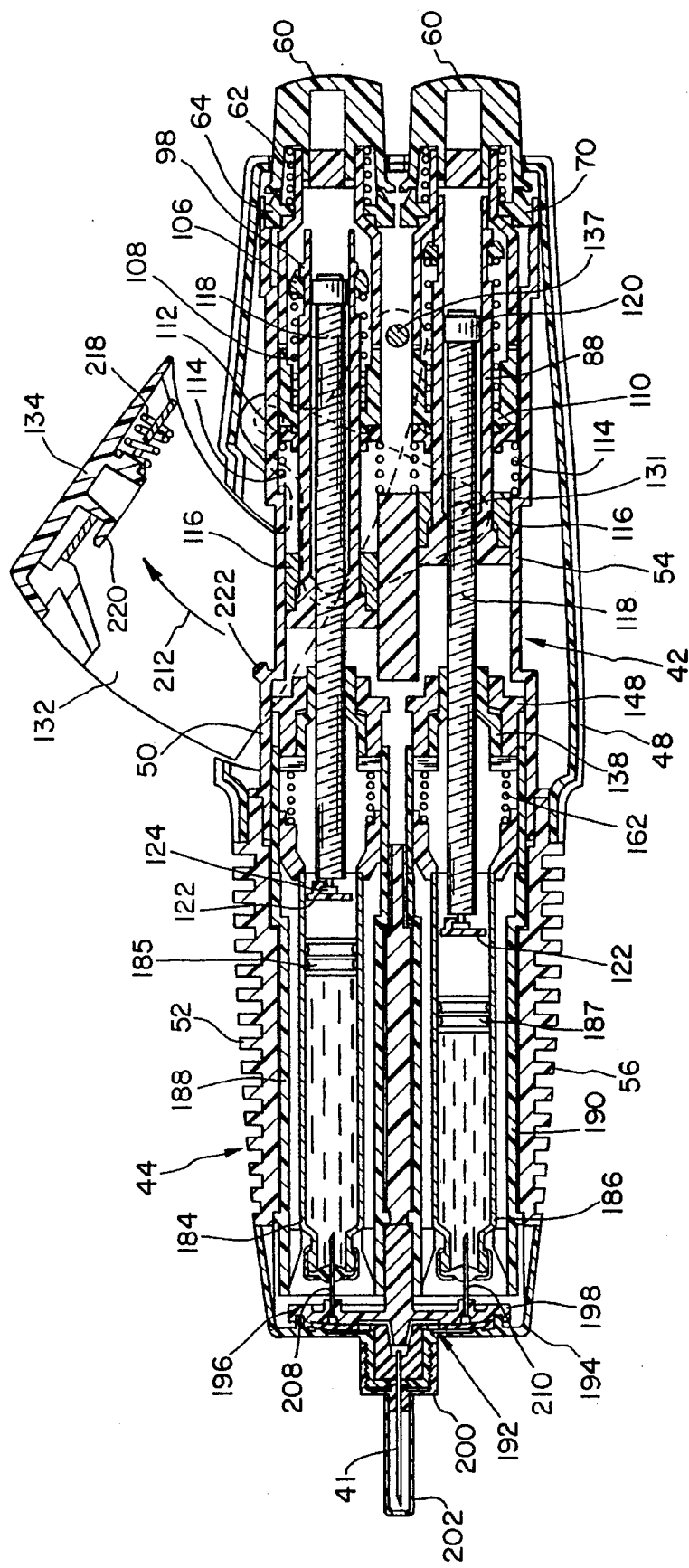
FIG. 3 is an enlarged longitudinal sectional view of the medication dispensing device of FIG. 1, wherein the actuating wing is in the "up" position.
Figure 4:
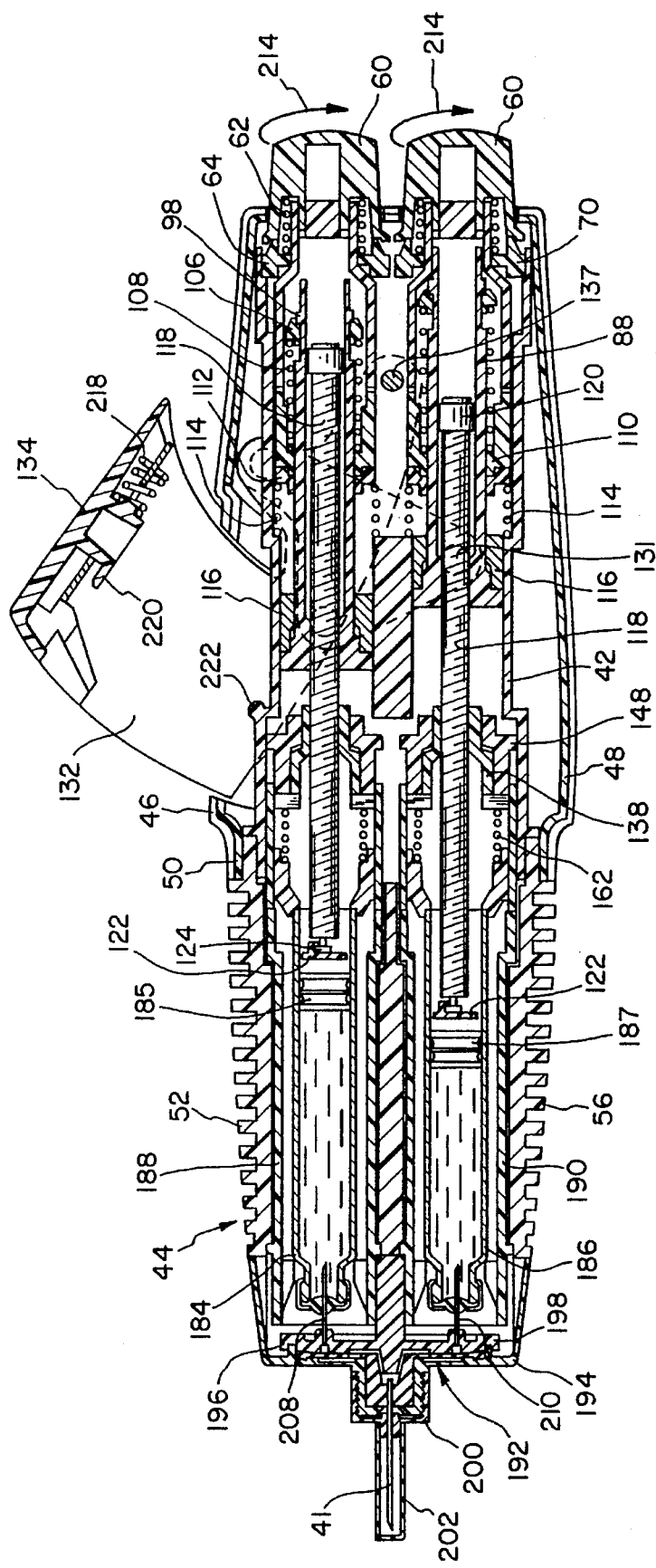
FIG. 4 is a view of FIG. 3, showing the leadscrews advanced indicating a set dosage has been established.
Figure 5:
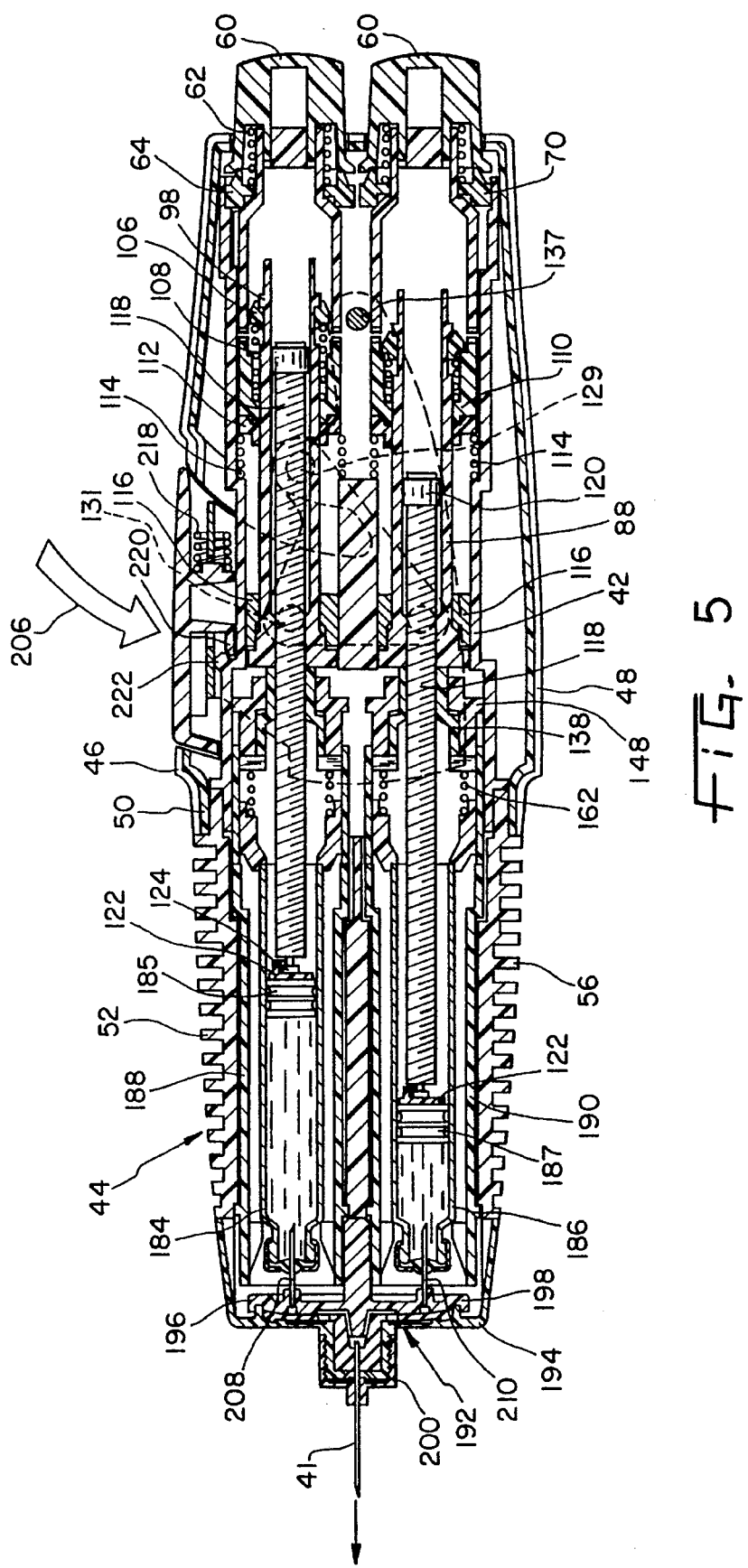
FIG. 5 is a view of FIG. 3, particularly showing the dispensing device immediately after an injection has taken place.

As shown in the drawings, dispensing device 40 contains two independent dosage metering mechanisms, a drive mechanism for simultaneously driving the pistons of the cartridges for dual medication injection, and two separate lock and pullback mechanisms. A detailed discussion of each mechanism follows. The two metering mechanisms shown in FIGS. 3–5 are substantially identical except for certain differences illustrated in FIG. 13. Likewise, the drive mechanism and the lock and pullback mechanisms within each tubular member are substantially identical to one another. Therefore, identical components in each of the two parallel tubular members formed by mechanism housing 42 and nosepiece 44 are given identical reference numerals.

Referring to FIGS. 2–6, a dosage metering mechanism 58 is shown. Although a single metering mechanism shall be discussed herein, it is understood that delivery mechanism 40 includes two such metering mechanisms. Metering mechanism 58 comprises a knob 60, a torsion spring 62, an indicator bearing 64, an indicator dial 66, and a clutch indicator 68. Indicator bearing 64 is a thin, molded plastic annular ring with hook-shaped protrusions 70 extending radially away from its outer circumference. As shown in FIG. 3, protrusions 70 securely fit within openings 71 (FIG. 2) formed at the proximal end of mechanism housing 42. Thus, indicator bearing 64 is fixed both rotationally and axially to mechanism housing 42. For purposes of this application, the term "proximal" shall designate a relative axial position toward the knob end of delivery mechanism 40, and the term "distal" shall designate a relative axial position toward the delivery needle end of delivery mechanism 40.

As shown in FIGS. 2 and 3, indicator dial 66 is an elongate molded plastic cylinder that fits coaxially within tubular region 54 of mechanism housing 42. Knob 60 is a molded plastic cylinder with a closed proximal end and an open distal end. The proximal end of indicator dial 66 snaps into an annular groove (not shown) molded within knob 60 so that indicator dial 66 and knob 60 constitute a single rotatable component. Torsion spring 62 is coupled at one end 72 to indicator dial 66 and at the opposite end 74 to indicator bearing 64. Knob 60 and indicator dial 66 are rotated against the biasing force of torsion spring 2. In the absence of another force to retain knob 60 and indicator dial 66 in a given radial position, torsion spring 62 will return knob 60 and indicator dial 66 to a given initial rotational position, also known as the zero dose position.

Figure 6:
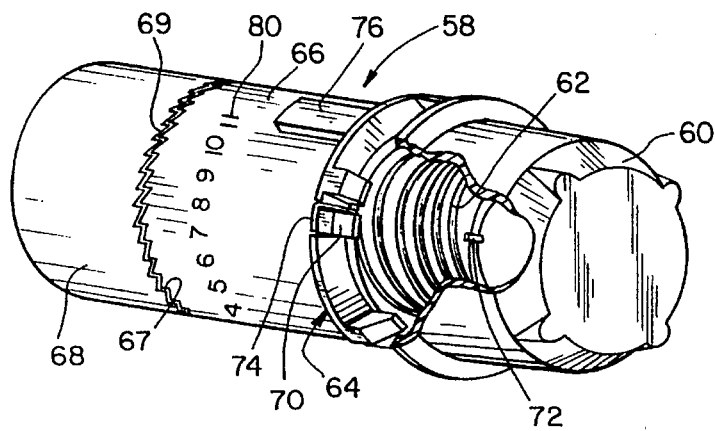
FIG. 6 is an enlarged isolated perspective view of the metering mechanism of the device of FIG. 1.
Figure 13:
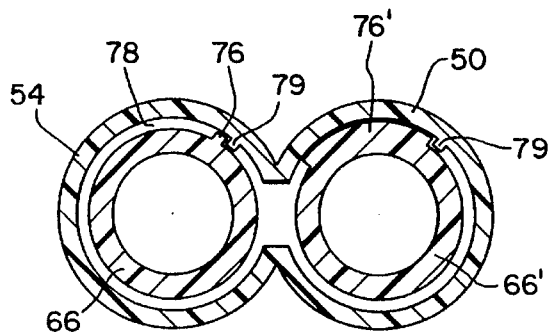
FIG. 13 is a sectional view of the indicator dial in engagement with the maximum dosage splines in the injection pen housing.

As shown in FIGS. 6 and 13, indicator dial 66 further includes an axially extending spline 76 which rotates within a mating slot 78 on the inside surface of tubular region 54 to confine the rotational travel of indicator dial 66 to less than 360 degrees. This serves to limit the dosage that a user can set for any single injection. In FIG. 13, there is shown an indicator dial 66' which is identical to indicator dial 66 except that spline 76' is of a greater width than spline 76. Thus, the maximum dosage that can be set with indicator dial 66' is less than that which can be set with indicator dial 66.

Referring to FIG. 6, the distal portion of indicator dial 66 has a series of numerals 80 printed about the circumference thereof. An opening or window 82 in the wall of tubular region 54 and a corresponding opening 84 in housing cover 48 allows a user to view at least one of numerals 80. A lens 86 (FIG. 2) is provided in opening 84 to magnify the visible numeral 80 as desired. The numerals represent different set dosages of liquid medication to be delivered in international recognized units. As the knob 60 and indicator dial 66 are rotated, different numerals 80 appear centered in openings 82 and 84. The reference numeral "0" is present when knob 60 and indicator dial 66 are in their initial position set by torsion spring 62. The metering mechanism interfaces with the drive mechanism as discussed infra.

Figure 7:
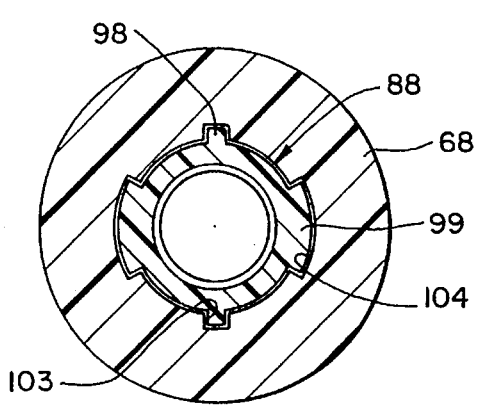
FIG. 7 is a sectional view of the engagement between the rotatable clutch member and the elongated nut.
Figure 8:
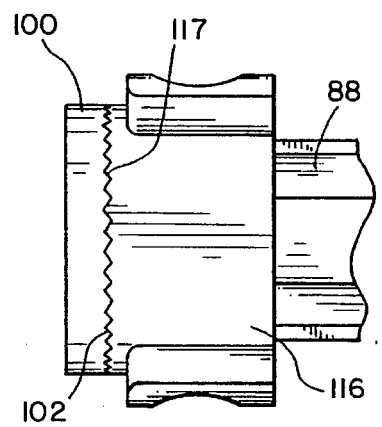
FIG. 8 is an isolated elevational end view of the nut and the driver, particularly showing the ratchet teeth of the nut in engagement with the corresponding ratchet teeth of the driver.
Figure 9:
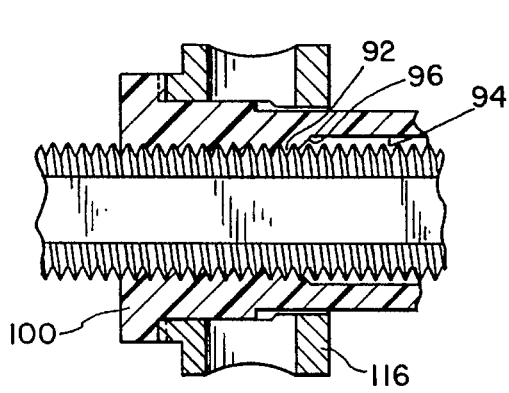
FIG. 9 is a sectional view showing the externally threaded leadscrew in engagement with the internally threaded portion of the nut.
Figure 10:
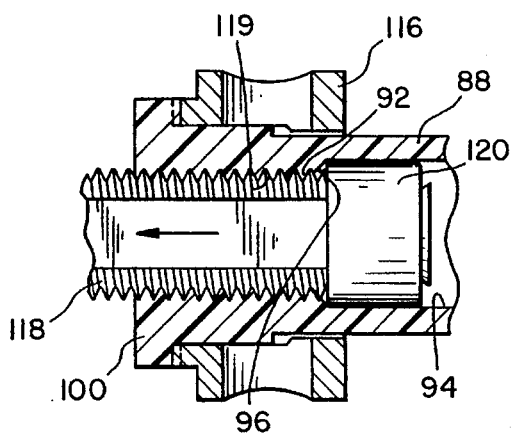
FIG. 10 is a view of FIG. 9, particularly showing the leadscrew fully advanced through the nut.
Figure 11:
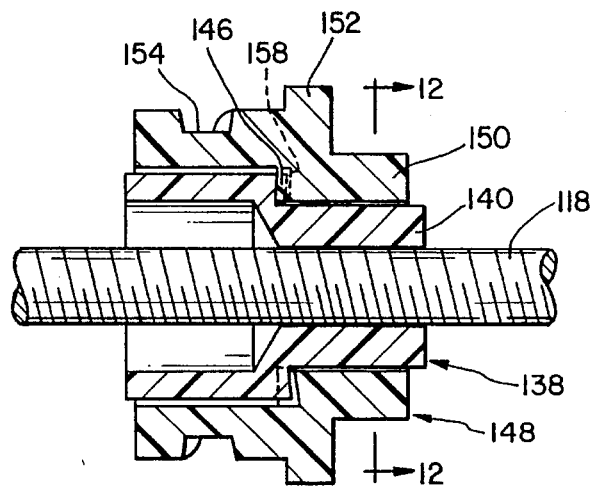
FIG. 11 is an enlarged sectional view of the assembled lock and pullback mechanism of the device of FIG. 1.
Figure 12:
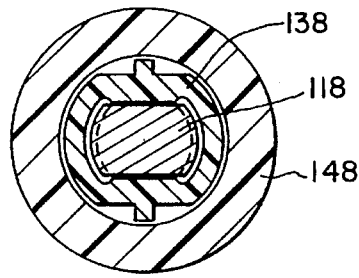
FIG. 12 is an enlarged sectional view of the lock and pullback mechanism as shown in FIG. 11, taken along line 12—12 in FIG. 11.

Referring to FIG. 2, the components of the drive mechanism are shown. The drive mechanism includes an elongated molded plastic, hollow cylindrical drive nut 88. Nut 88 includes an internally tapped bore extending therethrough. As shown in FIGS. 9 and 10, the distal portion 90 of nut 88 includes internal threads 92. These threads may be any desired helix, such as a 28–45 degree helix. The remaining interior surface of the bore of nut 88 constitutes a relatively smooth surface 94. A shoulder or ledge 96 is formed at the intersection between smooth interior surface 94 and internally threaded surface 92. Referring to FIG. 7 the outer surface of nut 88 includes a plurality of axially extending splines 98 and 99. These splines engage corresponding recesses 103 and 104 in indicator clutch 68, thereby locking nut 88 to indicator clutch 68. Referring to FIG. 8, the distal end of nut 88 includes an enlarged diameter end 100 including ratchet teeth 102. Referring to FIGS. 2–5, a drive spring 108 is disposed between the distal end of drive locknut 106 and the distal end 110 formed in the interior of indicator clutch 68. An indicator washer 112 is secured to indicator clutch 68, and an indicator spring 114 is disposed between washer 112 and tubular region 54 of housing 42.

An elongated metal externally threaded leadscrew 118 is adapted to threadingly engage the interior threaded surface 92 of drive nut 88. Leadscrew 118, while generally cylindrical, has two diametrically opposite parallel flat surfaces 126 (FIG. 2) extending along its entire length. Leadscrew 118 is longer than drive nut 88, and when assembled, the proximal end of leadscrew 118 extends beyond the threaded portion of drive nut 88. The proximal end of leadscrew 118 includes an enlarged diameter portion 120. A plastic head 122 is slidably snapped onto end piece 124 of leadscrew 118. Head 122 is rotatably attached to end piece 124 and is pivotal with respect thereto.

As shown in FIGS. 3–4, the metering mechanism is coupled to the drive mechanism. Specifically, ratchet teeth 67 of indicator dial 66 are in engagement with ratchet teeth 69 of indicator clutch 68. Thus, rotation of knob 60 results in rotation of indicator clutch 68. Since the splines 98, 99 of drive nut 88 are keyed to grooves 103, 104 in indicator clutch 68, rotation of indicator clutch 68 results in rotation of nut 88. Leadscrew 118 is locked against rotation during metering as shall be discussed infra. Since nut 88 is locked to the drive mechanism and cannot move axially with respect to the housing during metering, rotation of nut 88 causes axial translation of leadscrew 118 due to the threaded connection therebetween. After an initial desired dosage has been set, knob 60 may be turned either clockwise or counterclockwise to translate leadscrew 118 either forward or backward until the desired dosage is set. This allows a user to change a dosage without wasting the medication to be delivered.

Figure 24A:
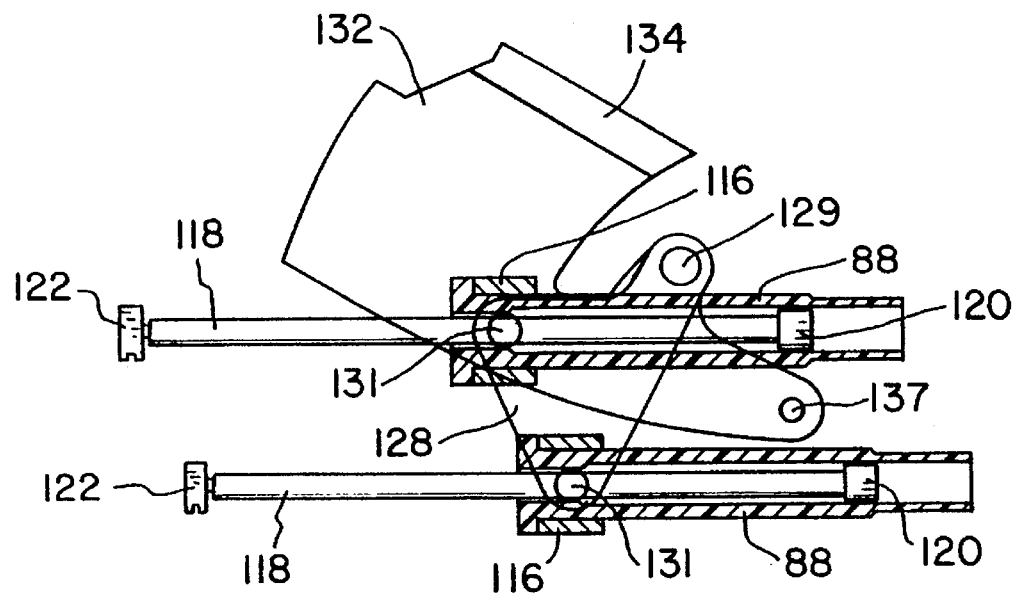
FIG. 24A is an isolated view, in partial section, of the wing and driver mechanism of the device of FIG. 1, showing the wing in its "up" position.
Figure 24B:
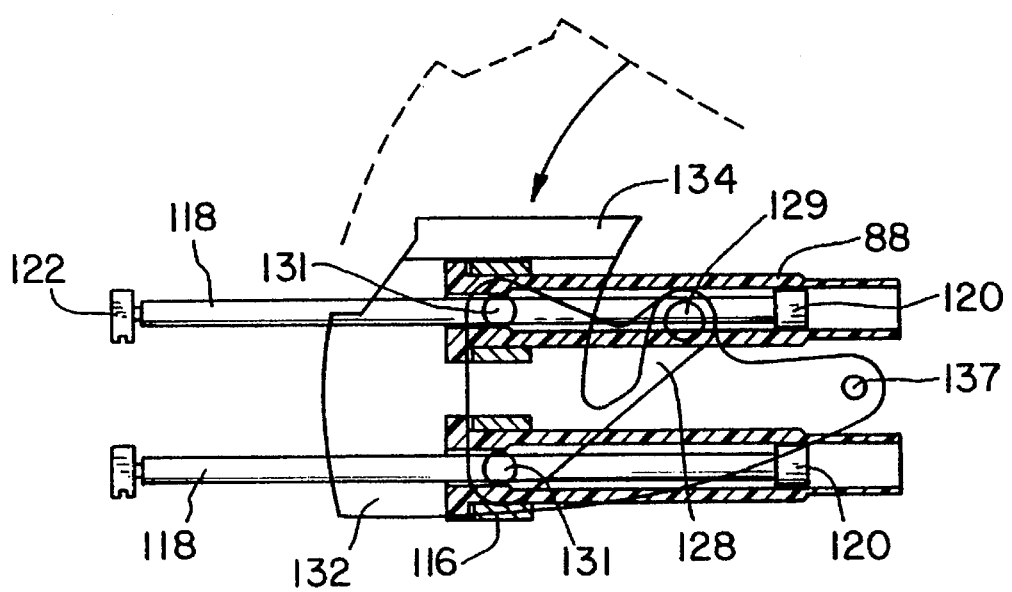
FIG. 24B is a view of FIG. 24, except that the wing is in its "down" position.

Referring to FIGS. 9 and 10, a carrier or driver 116 is in constant engagement with distal end 100 of drive nut 88. As shown in FIGS. 2, 24A and 24B, driver 116 is secured to plates 128 which are pivotally connected to wing 132 by pins 129 being received in pivot bores 133. Wing 132 includes a plastic grip 134 which is received within opening 136 within wing 132, as shown in FIG. 2. Wing 132 includes pivot bores 135, which receive opposite ends of a pivot pin 137 which extends through opening 139 in housing mechanism 42. Bores 127 in drivers 116 receive pins 131 of side plates 128. Referring to FIGS. 24A and 24B, upon movement of wing 132 toward mechanism housing 42 to its "down" position (FIG. 24B), side plates 128 and 130 are carried forwardly, which carry respective drivers 116 forwardly. Since each driver 116 is adjacent end 100 of nut 88, movement of driver 116 carries forward nut 88 and leadscrew 118. Upon movement of wing 132 away from mechanism housing 42 to its "up" position (FIG. 24A), side plates 128 and 130, driver 116, nut 88 and leadscrew 118 are all retracted.

The lock and pullback mechanism comprises a plastic molded, generally cylindrical pullback key 138 which has a proximal portion 140 including an opening 142 that corresponds to the shape of leadscrew 118 and an enlarged distal portion 144 including ratchet teeth 146. The lock and pullback mechanism further comprises a generally cylindrical molded pullback sleeve 148 comprising a proximal hollow cylindrical portion 150 and radially extending flanges 152. The outer surface of pullback sleeve 148 includes a spiral groove or track 154. The interior surface of pullback sleeve 148 including a reduced diameter inner surface 156 and an enlarged inner diameter surface (not shown). The intersection of the inner surfaces of pullback sleeve 148 form ratchet teeth 158 which are engageable with ratchet teeth 146 of pullback key 138. The lock and pullback mechanism further includes a lock key 160, a pullback spring 162, and a snap lock 164. Lock key 160 comprises a generally cylindrical portion 166 having grooved openings 168 formed at the distal end thereof and further having axially extending fingers 170 extending from the opposite end thereof. Fingers 170 include small cylindrical protrusions 172 that fit within spiral groove 154 of pullback sleeve 148. Lock key 160 further includes ledges 174 extending radially inwardly from the inner surface of lock key 160.

Snap lock 164 comprises a cylindrical portion 176 and two axially extending legs 178 having outwardly extending tabs 180. Pullback spring 162 is disposed between inner ledge 182 of snap lock 164 and inner radially extending ledges 174 of lock key 160.

The lock and pullback mechanism performs several functions. First, pullback key 138 interfaces with leadscrew 118 to keep the leadscrew 118 from turning during metering and injection. Pullback key 138 is locked from rotation by the engagement of corresponding teeth from pullback sleeve 148 which, in turn, is constantly constrained from rotating by its interface with mechanism housing 42. Lock snap 164 and pullback spring 162 take up the variable position of the end of the glass cartridge. In addition, lock snap 164 holds the lock/pullback mechanism within the mechanism housing. Lock key 160 provides a lockout for the cartridge retainers so that the retainers can only be removed and inserted when the wing is in the "down" position. It is important to lock out cartridge change in the wing "up" position because for a proper leadscrew reset to occur, the plunger of the replacing cartridge needs to push the leadscrew back and the wing must pull the leadscrew off the plunger by a distance of at least the maximum dosing distance. Pullback sleeve 148 unloads the pullback key 138 during a cartridge change such that the leadscrew can spin freely back to its home position. The lock and pullback mechanism will be described in additional detail upon a description of the manner of use of device 40.

Referring to FIG. 2, injection device 40 includes cartridges 184, 186 disposed within cartridge retainers 188, 190. Retainers 188, 190 which may be made of a clear plastic material, such as Ektar, include internal ribs 189, 191 (FIGS. 21–22) to ensure proper alignment of the cartridges in the retainers. Retainers 188, 190 are secured within the tubular regions 52 and 56 of nosepiece 44 as discussed infra. Retainer 188 may be of a different size than retainer 190 so that retainer 188 cannot be inadvertently inserted into cylindrical tube 56, and vice versa. A manifold assembly 192 is secured to the distal end of cartridge retainers 188 and 190 and includes a front housing 194, a rear housing 196, and an elastomeric septum 198 encapsulated therebetween. The manifold assembly is described in greater detail in U.S. patent application Ser. No. 08/333,207, filed Nov. 2, 1994, entitled MANIFOLD FOR INJECTION APPARATUS, which disclosure is incorporated herein by reference. Needle 41 is secured to front manifold housing 194 via threaded coupling member 200. Injection device 40 further includes needle cover 202 and housing cap 204.

In order to set a dosage, wing 132 must be moved in the direction of arrow 212 to its "up" position, as shown in FIG. 3. This causes heads 122 of leadscrews 118 to be retracted out of engagement with pistons 185, 187 of cartridges 184, as shown in FIG. 3. In addition, movement of wing 132 in the direction of arrow 212 retracts clutch indicator 68 to its proximal position. While in this position, ratchet teeth 67 of indicator dial 66 are in engagement with ratchet teeth 69 of indicator clutch 68 so that rotation of knob 60 and indicator dial 66 results in corresponding rotation of indicator clutch 68. As indicator clutch 68 is rotated, internal threads 92 of clutch 68 engage with external threads 119 of leadscrew 118 to cause axial translation of leadscrew 118 toward piston 185. Leadscrew 118 is prevented from rotating due to ratchet teeth 146 of pullback key 138 being in locking engagement with ratchet teeth 158 of pullback sleeve 148. Since pullback sleeve 148 is keyed against rotation with respect to the housing, pullback key 138 and leadscrew 118 likewise cannot rotate with respect to the housing. As a result, rotation of nut 88 results in the nonrotational translation of leadscrew 118 toward piston 185, as shown in FIG. 4.

Rotation of each knob 60 must initially be in the clockwise direction, as indicated by arrows 214 (FIG. 4) to set a desired dosage. Initial rotation in the counterclockwise direction is prevented by the engagement of splines 76, 76' of indicator dials 66, 66' being in engagement with dosage stops 79 formed in tubular regions 50 and 54 (FIG. 13). Once an initial dosage has been set, that dosage may be increased or decreased as desired by clockwise or counterclockwise rotation of knobs 60. FIG. 4 shows leadscrews 118 being advanced a desired axial distance with respect to their axial positions in FIG. 3, indicating that dosages have been set. Rotation of knob 60 results in corresponding numerals 80 appearing in openings 82 and 84 of housings 42 and 48, respectively, to provide a visual indication of the desired dose. In addition, rotation of nut 88 results in teeth 102 of end 100 being moved over teeth 117 of driver 116, resulting in an audible click for each incremental increase or decrease in the set dosage.

Once the desired dosage of both medications has been set, needle cover 202 is removed from needle 41, and needle 41 is inserted into the user. Wing 132 is then grasped and move transversely towards the housing as shown by arrow 206 in FIG. 5. This results in drivers 116 moving forward which carry nuts 88 and leadscrews 118 forwardly a predetermined distance resulting in heads 122 engaging and axially advancing associated pistons 185, 187. This forces medication through cannulas 208, 210 and into manifold assembly 192 and subsequently out needle 41.

As wing 132 is pushed toward the housing, ratchet teeth 69 of clutch indicator 68 move out of engagement with ratchet teeth 67 of indicator dial 66, thereby enabling torsion spring 62 to rotate knob 60 and clutch indicator 66 to its initial rotational position, whereby the numeral zero appears through windows 82 and 84 in housings 42 and 48, respectively. This auto zero feature permits a user to redial another dose without having to first set the metering dial to zero.

Figure 14:
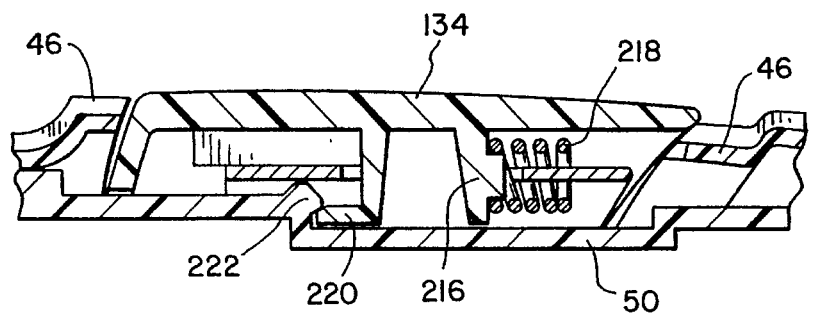
FIG. 14 is a sectional view of the wing mechanism of the dispensing device in engagement with the housing in its wing down position.
Figure 15:
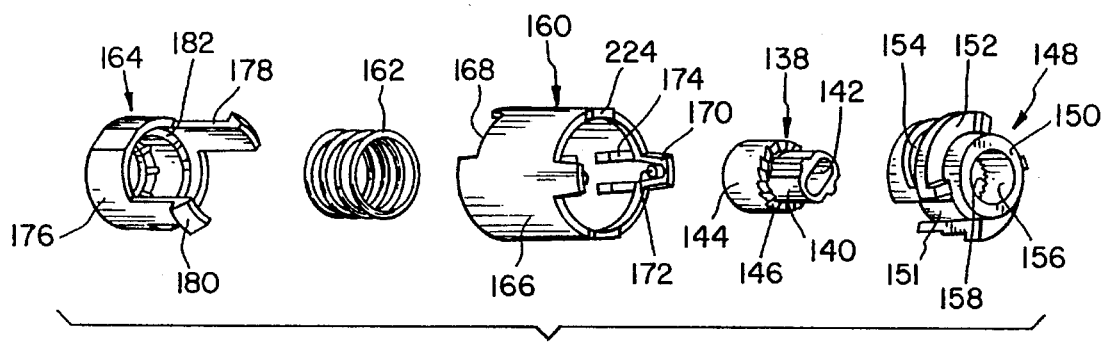
FIG. 15 is an exploded perspective view of the lock and pullback mechanism.
Figure 16:
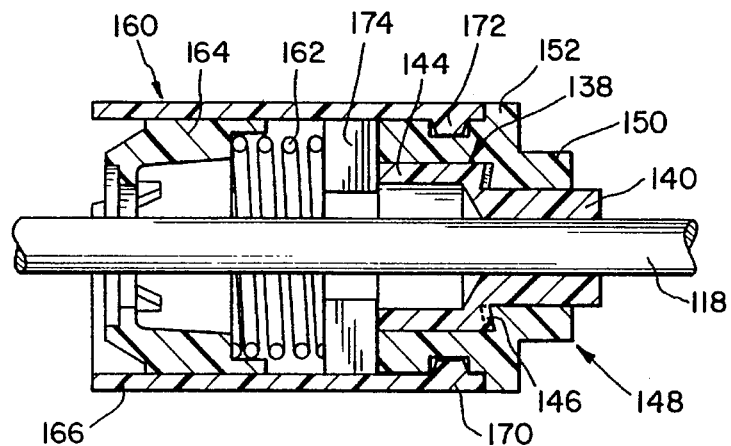
FIG. 16 is a sectional view of the assembled lock and pullback mechanism particularly showing the lock key within the groove of the pullback sleeve, thereby preventing rotation of the key with respect to the sleeve.
Figure 17:
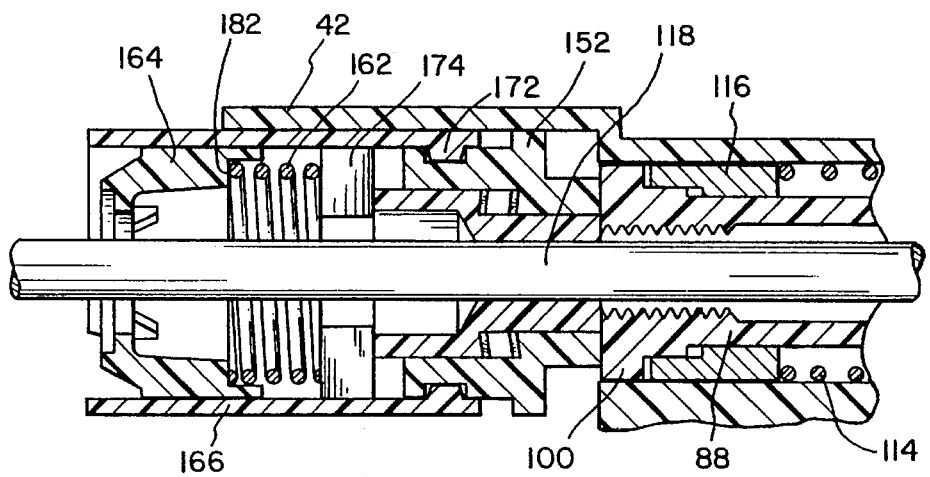
FIG. 17 is a view of the lock and pullback mechanism of FIG. 16, particularly showing the driver at the end of dose thereby automatically permitting rotation of the lock key with respect to the housing.
Figure 18:
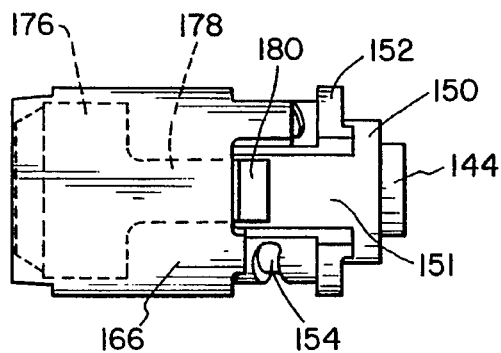
FIG. 18 is a sectional view of the interference fit between the small flanges of the lock key and the legs of the lock snap.

Referring to FIG. 14, grip piece 134 of wing 132 includes a downwardly extending boss portion 216 biased in a given axial position with respect to wing 132 by a spring 218. Boss 216 includes a finger 220 that slides over upstanding tab 222 on tubular region 50 and fits into place beneath tab 222 in interfering relationship therewith which holds finger 220 in place. This locks wing 132 in the "down" position at the end of dose. The engagement of finger 220 beneath tab 222 results in an audible click sound, indicating to the user that the complete dosage has been delivered. Spring 218 biases finger 220 beneath tab 222.

Figure 19:
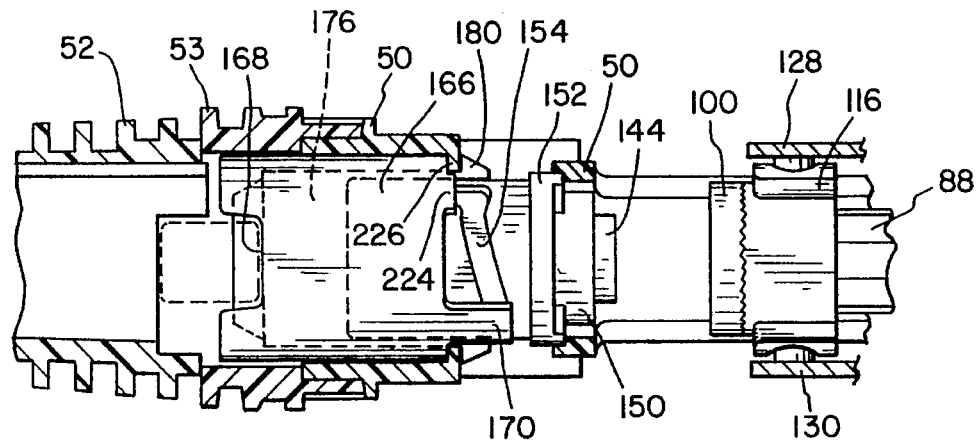
FIG. 19 shows the legs of the lock snap in engagement with the small flanges.
Figure 20:
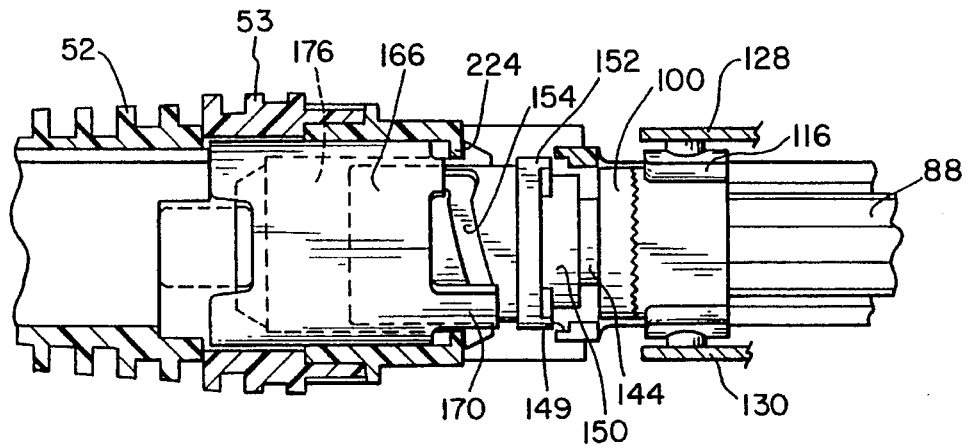
FIG. 20 is a view similar to FIG. 19, showing the lock snap out of engagement with the small flanges of the lock key to permit rotation of the lock key with respect to the pullback sleeve.

At the end of an injection, end 100 of nut 88 engages and axially advances pullback sleeve 148, pullback key 138 and lock key 160, as shown in FIGS. 19 and 20. This moves flanges 152 of pullback sleeve 148 out of engagement with groove 149 in tubular housing region 50. This also moves protrusion 224 on lock key 160 out of interfering relationship with extension 226 of tubular region 50. Cartridge retainer 188 and lock key 160 keyed thereto can now be rotated 90 degrees to move protrusions 172 of lock key 160 within helical spline 154 of pullback sleeve 148. Such rotation moves lock key 160 and ledges 174 of lock key 160 axially away from pullback key 138 so that ledges 174 no longer engage pullback key 138. This causes ratchet teeth 146 of pullback key 138 to become disengaged from ratchet teeth 158 of pullback sleeve 148, thereby enabling pullback key 138 and hence leadscrew 118 to rotate with respect to pullback sleeve 148 and mechanism housing 42.

Figure 21:
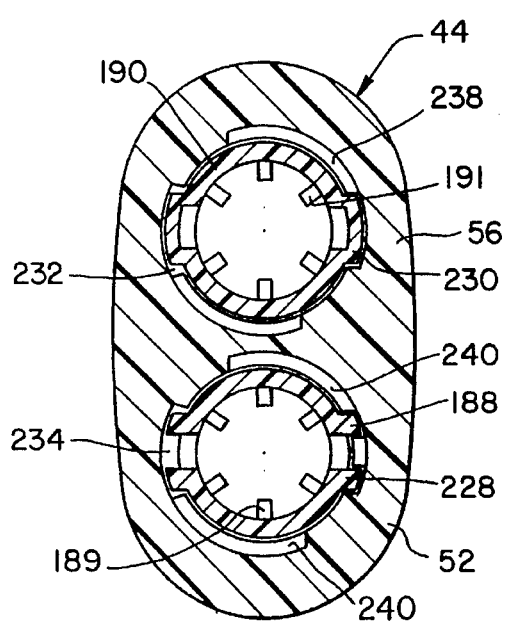
FIG. 21 is a sectional view of the cartridge retainers in the distal housing of the medication dispensing device of FIG. 1, particularly showing the retainers in an unlocked state.
Figure 22:
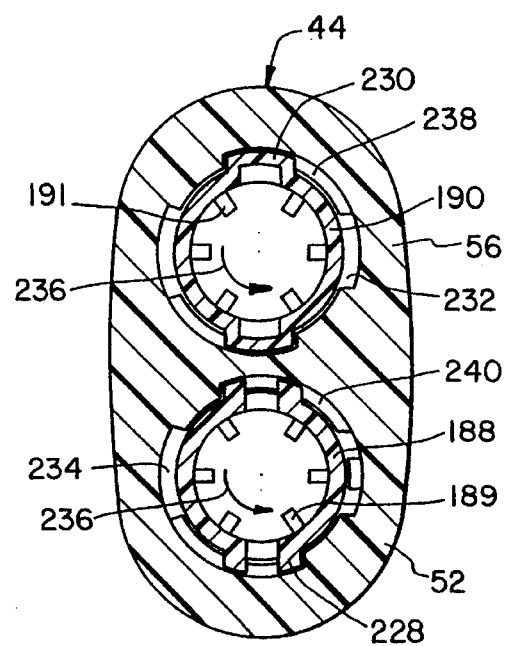
FIG. 22 is a view of FIG. 21, except that the cartridge retainers have been rotated to their locked positions.

As shown in FIGS. 20 and 21, the inner surfaces of tubular regions 52 and 56 of nosepiece 44 are specially configured to restrict cartridge retainers 188, 190 to a particular radial orientation therewithin. Specifically, keyed portions 228, 230 of retainers 188, 190, respectively, rotate within grooves 232, 234 formed in the proximal end of nosepiece 44. Each groove 232, 234 extends for 90 degrees about the circumference of the openings in nosepiece 44, thereby limiting rotation of retainers 188, 190 to 90 degrees within nosepiece 44. In addition, retainers 188, 190 can be removed from nosepiece 44 only in a particular radial orientation. Referring to FIG. 21, retainers 188, 190 are shown in their unlocked radial positions. In FIG. 22, retainers 188, 190 have been rotated 90 degrees counterclockwise in the direction of arrows 236 to cause the top edge surfaces of keyed portions 228, 230 to be in engagement with interfering internal threads 238, 240, respectively, thereby preventing the retainers 188, 190 from being axially removed from nosepiece 44. Thus, retainers 188, 190 are shown in their locked radial positions in FIG. 22.

Referring to FIG. 10, an insufficient dose remaining feature is shown. In particular, if a user dials up a dosage greater than that remaining in its cartridge, enlarged portion 120 of leadscrew 118 engages ledge 96 of internally threaded nut 88. This provides an interference stop that prevents leadscrew 118 from being translated any further. This indicates to the user that there is an insufficient dosage remaining in the cartridge. At this point, the user may choose to inject the dosage already set and then dial up the difference after inserting a new cartridge.

Figures 23A, 23B, 23C:
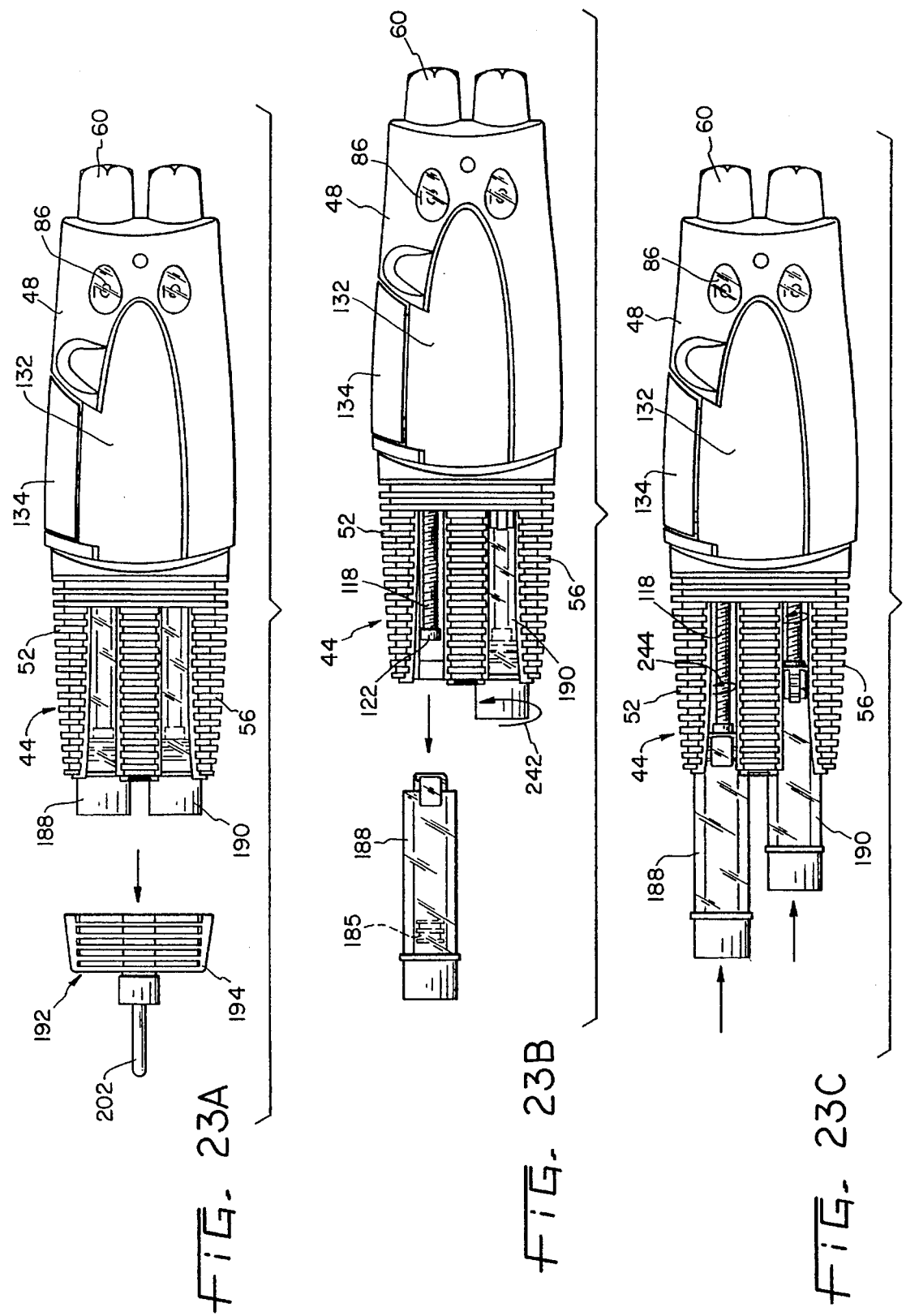
FIGS. 23A–23D are a series of elevational views of the medication dispensing device of FIG. 1 showing the manifold being removed (FIG. 23A), the cartridge retainers being unlocked and removed from the housing (FIG. 23B), new cartridge retainers being inserted into the housing (FIG. 23C) and the manifold being replaced onto the distal end of the housing (FIG. 23D).
Figure 23D:
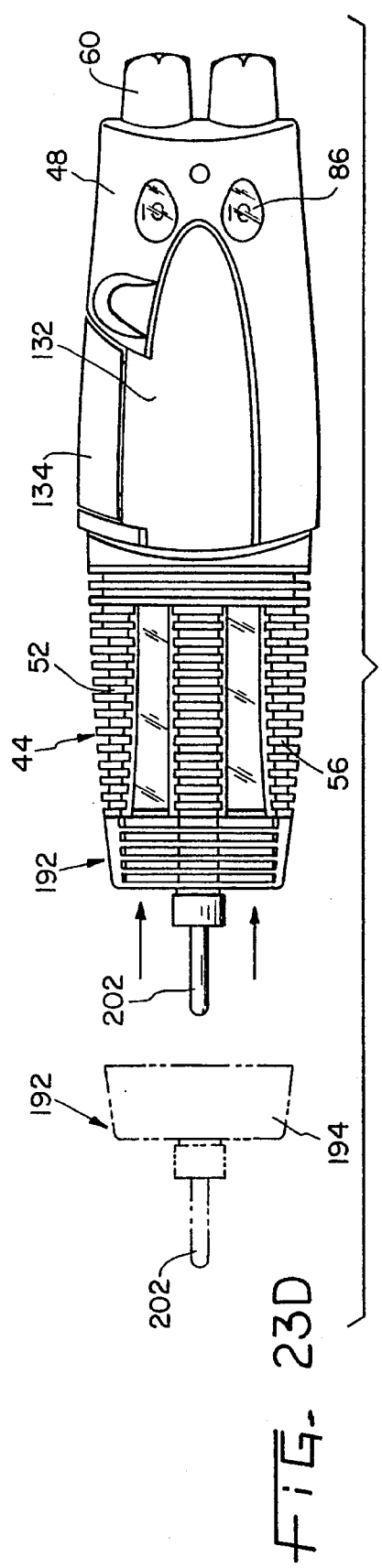

The process for changing a spent cartridge is illustrated in FIGS. 23A–23D. It will be appreciated that the process of changing cartridges can occur only while wing 132 is in its "down" position. First, manifold 192 is removed from cartridge retainers 188, 190 and from the distal end of nosepiece 44, as shown in FIG. 23A. Next, retainers 188, 190 are rotated 90 degrees as indicated by arrow 242, and then removed. The spent cartridges are then removed from the retainers, and new cartridges are inserted therein. Retainers 188, 190 are then inserted back into nosepiece 44, as shown in FIG. 23C. The pistons of the new cartridges engage heads 122 of leadscrews 118 and force leadscrews to rotate as indicated by arrows 244 in FIG. 23C. Leadscrews 118 are spun back to their home positions. Once keyed portions 228, 230 of retainers 188, 190, respectively, are fully seated within respective lock keys 160, retainers 188, 190 are rotated to lock them into place. Finally, manifold 192 is inserted back onto the distal end of nosepiece 44 over retainers 188, 190, as shown in FIG. 23D.

In order to make a subsequent injection, wing 132 must be moved to its "up" position (FIGS. 1, 24A) in the direction of arrow 212, as shown in FIG. 3. This is necessary in order to cause ratchet teeth 69 of clutch indicator 68 to engage ratchet teeth 67 of indicator dial 66 so that rotation of knob 60 results in rotation of nut 88.

It will be appreciated that the foregoing is presented by way of illustration only, and not by way of any limitation, and that various alternatives and modifications may be made to the illustrated embodiment without departing from the spirit and scope of the invention.

What is claimed is:

1. An apparatus for the delivery of an injectable product, comprising:

a housing;

a container mounted to said housing and including a piston, an exit and an injectable product between said piston and said exit;

a drive stem disposed in said housing and engageable with said piston;

a tubular element threadably coupled to said drive stem such that said tubular element is rotatable with respect to said drive stem, wherein relative rotation between said tubular element and said drive stem controls the amount of telescopic extension of said drive stem from said tubular element to establish a set dosage of injectable product to be delivered, wherein a first coupling element is secured to said tubular element for rotation with said tubular element;

a drive assembly secured to said tubular element and movable with respect to said housing between a pre-injection position and a post-injection position for axially moving said drive stem with respect to said housing, to drive said piston within said container upon movement of said drive assembly from said pre-injection position to said post-injection position; and a user-engageable dose setting assembly including a second coupling element engageable with said first coupling element for rotation with said first coupling element to enable a user to effect said relative rotation between said tubular element and said drive stem, wherein said first coupling element is in engagement with and rotatable with said second coupling element while said drive assembly is in said pre-injection position, and said first coupling element is axially spaced from said second coupling element while said drive assembly is in said post-injection position, thereby preventing a user from setting a dose while said drive assembly is in its post-injection position.

2. The apparatus of claim 1, wherein said piston is axially movable in said container toward said exit to define an axis of ejection of said injectable product, wherein said drive assembly includes an actuator movable in a direction transverse to said axis of ejection for moving said drive assembly between said pre-injection position and said post-injection position.

3. The apparatus of claim 1, wherein said dose setting assembly is rotatable between an initial radial position and a final radial position for establishing said set dosage of injectable product to be delivered while said drive assembly is in said pre-injection position, wherein a spring is secured to both said housing and said dose setting assembly for automatically biasing said dose setting assembly to said initial radial position upon movement of said drive assembly from said pre-injection position to said post-injection position.

4. The apparatus of claim 3, wherein said dose setting assembly comprises a sleeve-like indicator dial, wherein a first axial end of said dial is secured to a user-engageable knob and a second axial end of said dial comprises a set of ratchet teeth for engagement with said first ratchet element of said drive assembly.

5. The apparatus of claim 4, wherein said dose setting assembly includes a bearing element between said knob and a portion of said dial, said bearing element being secured to said housing and said knob and dial being rotatable with respect to said bearing element, wherein a first end of said spring is secured to said bearing element and a second end of said spring is secured to one of said knob and said dial.

6. The apparatus of claim 4, wherein said dial includes a plurality of numerals spaced thereabout, wherein said housing includes an opening therein and said dial is arranged in said housing such that a numeral appears in said opening, thereby indicating to the user the number of dosage units constituting said set dosage.

7. The apparatus of claim 6, wherein the numeral 0 appears in said opening while said dose setting assembly is in said initial radial position.

8. An apparatus for the delivery of an injectable product, comprising:

a housing;

a container mounted to said housing and including a piston, an exit and an injectable product between said piston and said exit;

a tubular element disposed in said housing, said tubular element including an internally threaded surface;

a drive stem telescopingly extending through said inner diameter surface and including a first axial end engageable with said piston, a second and opposite axial end comprising an enlarged diameter portion, and an externally threaded surface between said first end and said second end, said externally threaded surface in engagement with said internally threaded surface of said tubular element;

a nut secured to said drive stem for restraining rotation of said drive stem upon rotation of said tubular element, said drive stem being axially movable with respect to said tubular element upon rotation of said tubular element, wherein relative rotation between said tubular element and said drive stem controls the amount of telescopic extension of said drive stem from said tubular element to establish a set dosage of injectable product to be delivered, wherein said amount of telescopic extension of said drive stem from said tubular element is at a maximum upon said enlarged diameter portion of said drive stem engaging said internally threaded surface of said tubular element; and a drive assembly coupled to said drive stem for axially moving said drive stem to drive said piston.

9. The apparatus of claim 8, wherein said drive assembly is secured to said tubular element, said tubular element being axially stationary upon rotation of said tubular element.

10. An apparatus for the delivery of an injectable product, comprising:

a housing;

a container mounted to an end of said housing and including a piston, an exit and an injectable product between said piston and said exit;

a drive stem disposed in said housing and drivingly coupled to said piston;

a drive assembly coupled to said drive stem for moving said drive stem to drive said piston within said container;

a rotatable piece secured to said drive stem for rotation with said drive stem;

a locking sleeve disposed about said drive stem and coupled to said rotatable piece to restrict rotation of said rotatable piece, said rotatable piece and said locking sleeve being in engagement with one another while said container is mounted to said housing to prevent rotation of said rotatable piece and said drive stem; and a disengaging mechanism coupled to at least one of said rotatable piece and said locking sleeve for automatically disengaging said locking sleeve from said rotatable piece upon removal of said container from said housing, thereby permitting said rotatable piece and said drive stem to be rotated with respect to said housing.

11. The apparatus of claim 10, wherein said disengaging mechanism comprises a locking device keyed to said locking sleeve and movable between a locked position and an unlocked position, wherein in said locked position, said locking device is in tight engagement with said rotatable piece thereby forcing said rotatable piece into locking engagement with said locking sleeve for preventing rotation of said rotatable piece and drive stem, and wherein in said unlocked position, said locking device is spaced from said rotatable piece, thereby permitting said rotatable piece to be spaced from said locking sleeve, thereby enabling rotation of said rotatable piece and said drive stem with respect to said housing.

12. The apparatus of claim 11, including a holder for said container, said holder including means for rotating said locking device between said locked position and said unlocked position.

13. The apparatus of claim 12, including means for securing said holder to said locking device while said locking device is in said locked position.

14. The apparatus of claim 11, including means for locking said locking device in said locked position.

15. The apparatus of claim 10, wherein said rotatable piece includes a first set of ratchet teeth and said locking sleeve includes a second set of ratchet teeth, wherein said first set of ratchet teeth are in engagement with said second set of ratchet teeth upon engagement with one another.

16. An apparatus for effecting delivery of an injectable product, comprising:

a housing;

a cartridge received in said housing for containing and sealing an injectable product therein, said cartridge including an exit end and a piston axially movable in said cartridge to define an axis of ejection of the injectable product from said cartridge;

a manually adjustable dosage metering mechanism rotatably disposed in said housing for enabling a user to selectively set a dosage of the injectable product to be delivered without effecting delivery of the injectable product from said cartridge, said dosage metering mechanism including a dial having a first stop member, wherein said housing includes a second stop member, said first stop member engageable with said second stop member to limit rotation of said dial to less than 360° to thereby establish a-maximum dosage setting; and a delivery mechanism for engaging and axially advancing said piston a distance sufficient to cause said set dosage to be delivered out of said cartridge, said delivery mechanism including a hand operated actuator.

17. A medication dispensing device for effecting the simultaneous delivery of two injectable products, comprising:

a housing;

a first cartridge received in said housing and containing and sealing a first injectable product therein, said first cartridge having a first exit end and including a first piston therein;

a second cartridge received in said housing and containing and sealing a second injectable product therein, said second cartridge having a second exit end and including a second piston therein;

a first dosage metering mechanism disposed in said housing and including a first dosage adjuster coupled to a first plunger-engageable member such that adjustment of said first dosage adjuster establishes a first set dosage of injectable product to be delivered;

a second dosage metering mechanism disposed in said housing and including a second dosage adjuster coupled to a second plunger-engageable member such that upon adjustment of said second dosage adjuster such that adjustment of said second dosage adjuster establishes a second distance with respect to said housing to establish a second set dosage of injectable product to be delivered;

a manifold secured to said first and second exit of said first and second cartridges, respectively, for enabling the mixing of said first and second set dosages of said first and second injectable products within said manifold upon delivery from said respective cartridges into said manifold, said manifold being in fluid communication with said first and second cartridges and containing a common exit for enabling the mixed injectable product to be delivered to a user; and a drive mechanism coupled to said first and second plunger-engageable members for simultaneously axially advancing said first and second members a distance sufficient to engage and axially advance said first and second pistons, respectively, to effect simultaneous delivery of said first and second set dosages into said manifold and out through said common exit, said drive mechanism moveable to axially retract said first and second plunger-engagement members away from said respective first and second pistons after said delivery of said mixed injectable product.

18. The dispensing device of claim 17, wherein said first dosage metering mechanism is coupled to said first plunger-engageable member such that upon adjustment of said first dosage adjuster, said first member is axially advanceable a first distance with respect to said housing to establish said first set dosage of injectable product to be delivered without effecting delivery of the first injectable product and said second dosage metering mechanism is coupled to said second plunger-engageable member such that upon adjustment of said second dosage adjuster, said second member is axially advanceable a second distance with respect to said housing to establish said second set dosage of injectable product to be delivered without effecting delivery of the second injectable product.

19. The dispensing device of claim 17, wherein said drive mechanism includes a carrier, wherein said first and second plunger-engageable members are secured to said carrier and axially movable therewith, said carrier being axially advanceable upon actuation of said injector mechanism to simultaneously advance said members to effect simultaneous delivery of said first and second set dosages.

20. The dispensing device of claim 17, wherein the axial advancement of said first and second pistons in said first and second cartridges, respectively, defines a first axis of delivery and a second axis of delivery, respectively, said first and second axes of delivery being generally parallel to one another, wherein said dispensing device includes a hand-operated actuator movable in a direction transverse to said axes of delivery to effect delivery of the mixed injectable product.

21. The dispensing device of claim 17, wherein said drive mechanism operates independently of said first and second metering mechanisms.

22. The dispensing device of claim 17, wherein said first and second dosage adjustors are rotatable to set said first and second dosages.

23. The dispensing device of claim 22, wherein said first and second dosage adjusters are rotatable in both a clockwise direction and a counterclockwise direction thereby enabling each of said respective first and second members to be translated axially forwardly and rearwardly to enable a user to selectively increase and decrease said first and second set dosages prior to actuating said injector mechanism.

24. The dispensing device of claim 17, wherein said first and second plunger-engageable members are leadscrews coupled to said respective first and second dosage metering mechanisms in such a manner that adjustment of each said respective dosage adjustor causes said respective leadscrew to translate axially in a non-rotary manner within said housing.

25. An apparatus for the delivery of an injectable product, comprising:

a housing;

a container mounted within said housing and including a piston, an exit and an injectable product between said piston and said exit;

a drive stem disposed in said housing and drivingly coupled to said piston;

a drive assembly mounted to said housing and axially movable in said housing between a dose-setting position and an injection position for moving said drive stem to drive said piston within said container, said drive assembly including a first ratchet element; and a dose setting assembly including a second ratchet element coupled to said first ratchet element to establish a set dosage of injectable product to be delivered, said dose setting assembly including an indicator element being movable from a zero dose reference position against a biasing force to a specific dose reference position upon the setting of a desired dose to be delivered, said first ratchet element being in engagement with said second ratchet element to maintain said indicator element in said specific dose position while said drive assembly is in said dose-setting position, said first ratchet element being movable out of engagement with said second ratchet element upon movement of said drive assembly from said dose-setting position to said injection position, thereby enabling said indicator element to be automatically biased by said biasing force back to its zero dose reference position.

26. An apparatus for the delivery of an injectable product, comprising:

a housing;

a container mounted to said housing and including a piston, an exit and an injectable product between said piston and said exit;

an internally threaded nut disposed in said housing and rotatable with respect to said housing, and an externally threaded leadscrew disposed in said nut and drivingly coupled to said plunger;

means secured to said leadscrew for restraining said leadscrew against rotation upon rotation of said nut so that rotation of said nut causes translation of said leadscrew;

a drive assembly mounted to said housing and axially movable in said housing between a pre-injection position and a post-injection position for moving said leadscrew to drive said piston within said container, said drive assembly including a clutch element secured to said nut for rotation therewith, said clutch element including a first ratchet element, said clutch element, nut, and leadscrew being axially movable between said pre-injection position and said post-injection position; and a dose setting assembly coupled to said drive assembly and comprising a rotatable element having a dose setting knob and a rotatable second ratchet element engageable with said first ratchet element while said drive assembly is in said pre-injection position so that rotation of said knob results in rotation of said nut, said rotatable element being rotatable against the force of a spring from an initial radial position to a selective final radial position for selectively advancing said leadscrew to set the dosage of injectable product to be delivered, said first ratchet element being spaced from said second ratchet element while said drive assembly is in said post-injection position, whereby said spring biases said rotatable element from said final radial position to said initial radial position upon movement of said drive assembly from said pre-injection position to said post-injection position.

27. The apparatus of claim 26, wherein said piston is axially movable in said container toward said exit to define an axis of ejection of said injectable product, wherein said drive assembly includes an actuator movable in a direction transverse to said axis of ejection for moving said drive assembly between said pre-injection position to said post-injection position.

28. The apparatus of claim 26, wherein said rotatable member includes a plurality of numerals spaced about said rotatable member, wherein said housing includes an opening therein and said rotatable member is arranged in said housing such that a numeral appears in said opening, thereby indicating to the user the number of dosage units constituting said set dosage.

29. The apparatus of claim 28, wherein the numeral 0 appears in said opening while said rotatable member is in its initial radial position.

30. An apparatus for the delivery of an injectable product, comprising:

a housing;

a container mounted to said housing and including a piston, an exit and an injectable product between said piston and said exit;

piston-engagement means disposed in said housing for drivingly engaging said piston;

drive means mounted to said housing for moving said piston-engagement means between a pre-injection axial position and a post-injection axial position, with respect to said housing, to drive said piston within said container, said drive means including a first ratchet element, and a nut means coupled to said piston-engagement means for rotation with respect to said piston-engagement means, wherein relative rotation between said nut means and said piston-engagement means controls the amount of telescopic extension of said piston-engagement means from said nut means to establish a set dosage of injectable product to be delivered, said piston-engagement means being axially movable with said nut means between said pre-injection position and said post-injection position; and dose setting means for setting a dosage of injectable product to be delivered, said dose setting means coupled to said drive means and comprising a rotatable element including a dose setting knob and a second ratchet element engageable with said first element while said drive means is in said pre-injection position, wherein said dose setting knob is coupled to said nut means while said piston-engagement means is in said pre-injection position so that rotation of said knob with respect to said housing results in rotation of said nut means, said rotatable element being rotatable against the force of a spring means from an initial radial position to a selective final radial position for selectively advancing said piston-engagement means to set the dosage of injectable product to be delivered, said first ratchet element being spaced from said second ratchet element while said piston-engagement means is in said post-injection position, whereby said spring means biases said rotatable element from said final radial position to said initial radial position upon movement of said piston-engagement means from said pre-injection position to said post-injection position.

31. The apparatus of claim 30, wherein said piston is axially movable in said container toward said exit to define an axis of ejection of said injectable product, wherein said drive means includes an actuator movable in a direction transverse to said axis of ejection for moving said piston-engagement means between said pre-injection position to said post-injection position.

32. The apparatus of claim 30, wherein said rotatable member includes a plurality of numerals spaced about said rotatable member, wherein said housing includes an opening therein and said rotatable member is arranged in said housing such that a numeral appears in said opening, thereby indicating to the user the number of dosage units constituting said set dosage.

33. The apparatus of claim 32, wherein the numeral 0 appears in said opening while said rotatable member is in its initial radial position.

34. An apparatus for the delivery of an injectable product, comprising:

a housing;

a container received in said housing and including a piston, an exit and an injectable product between said piston and said exit;

a drive stem disposed in said housing and drivingly coupled to said piston; and a drive assembly mounted to said housing and axially movable in said housing for moving said drive stem to drive said piston within said container;

wherein a locking mechanism is engageable with said drive stem and configured to restrict rotation of said drive stem with respect to said housing, said locking mechanism being in engagement with said drive stem while said container is securely mounted in said housing to prevent rotation of said drive stem with respect to said housing, said locking mechanism being automatically disengaged from said drive stem upon removal of said container from said housing, thereby permitting said drive stem to be rotated with respect to said housing.

35. An apparatus for the delivery of an injectable product, comprising:

a housing having a proximal end and a distal end;

a removable cartridge retainer received in said distal end of said housing;

a replaceable cartridge received in said cartridge retainer and including a piston, an exit and an injectable product between said piston and said exit, said cartridge retainer being removable to enable said cartridge to be replaced with another cartridge;

a drive stem disposed in said housing and drivingly coupled to said piston;

a dosage metering mechanism disposed in said housing to establish a first set dosage of the first injectable product to be delivered; and a drive assembly mounted to said housing and axially movable in said housing for moving said drive stem to drive said piston within said cartridge;

wherein an automatic lockout mechanism is engageable with said drive stem and configured to prevent axial movement of said drive stem toward said proximal end of said housing independent of said dosage metering mechanism and said drive assembly, said lockout mechanism being in engagement with said drive stem while said cartridge retainer is securely mounted in said housing to prevent said independent axial movement of said drive stem with respect to said housing, said lockout mechanism being automatically disengaged from said drive stem upon removal of said cartridge retainer from said housing, thereby permitting said drive stem to be axially moved toward the proximal end of said housing independent of said dosage metering mechanism and drive assembly.

36. The apparatus of claim 35, wherein said automatic lockout mechanism comprises a pullback key having an opening that generally matches the shape of said drive stem and is rotatable with said drive stem, a pullback sleeve that is rotationally fixed with respect to said housing and engageable with said pullback key, and a lock key that is rotatable between an unlocked position and a locked position, wherein in said locked position, said pullback key is in engagement with said pullback sleeve to prevent rotation of said pullback key with respect to said housing, and wherein in said unlocked position, said pullback key is rotatable with respect to said pullback sleeve, thereby enabling said independent movement of said drive stem.

37. An apparatus for the delivery of an injectable product, comprising:

a housing;

a removable cartridge retainer received in said housing;

a replaceable cartridge received in said cartridge retainer and including a piston, an exit, and an injectable product between said piston and said exit, said cartridge retainer being removable to enable said cartridge to be replaced with another cartridge;

a drive stem disposed in said housing and drivingly coupled to said piston;

a drive assembly mounted to said housing and axially movable in said housing for moving said drive stem to drive said piston with said cartridge;

a hand-operated actuator for moving said drive assembly between a pre-injection position and a post-injection position; and means for locking said cartridge retainer to said housing while said drive assembly is in one of said pre-injection and post-injection positions.

38. The apparatus of claim 37, wherein said cartridge retainer is locked to said housing while said drive assembly is in said pre-injection position.

39. The apparatus of claim 37, wherein said means for locking said container includes a lock key that is rotatable with respect to said housing while said drive assembly is in said post-injection position and said lock key is not rotatable with respect to said housing while said drive assembly is in said pre-injection position.

40. The apparatus of claim 39, wherein said cartridge retainer is keyed to said lock key such that said cartridge retainer is rotatable with said lock key.

41. An apparatus for the delivery of an injectable product, comprising:

a housing;

a cartridge retainer received in said housing;

a cartridge received in said cartridge retainer and including a piston, an exit and an injectable product between said piston and said exit;

a drive stem disposed in said housing and drivingly coupled to said piston; and a drive assembly mounted to said housing and axially movable in said housing for moving said drive stem to drive said piston within said cartridge;

a hand-operated actuator for moving said drive assembly between a pre-injection position and a post-injection position;

wherein a rotatable piece is secured to said drive stem for rotation therewith, and a locking sleeve is disposed about said drive stem and configured to restrict rotation of said rotatable piece with respect to said housing, said rotatable piece and said locking sleeve being biased in unlocked relationship with one another, said rotatable piece and said locking sleeve being forced into locked engagement with one another while said retainer is mounted to said housing to prevent rotation of said rotatable piece and said drive stem with respect to said housing, said rotatable piece and said locking sleeve being automatically disengaged from one another upon removal of said retainer from said housing, thereby permitting said rotatable piece and said drive stem to be rotated with respect to said housing.

42. The apparatus of claim 41, wherein a spring is positioned in said housing with respect to said rotatable piece and said locking means to apply a biasing force sufficient to separate a first locking element of said rotatable piece from a second locking element of said locking means, said spring means being positioned in said housing such that upon said container being secured to said housing end, said spring means is compressed sufficiently to permit said rotatable piece to lockingly engage with said locking means.

43. The apparatus of claim 41, wherein said rotatable piece includes a first set of ratchet teeth and said locking means includes a second set of ratchet teeth, wherein said first set of ratchet teeth are in engagement with said second set of ratchet teeth while said container is mounted to said housing.

44. The apparatus of claim 41, wherein said plunger-engagement means is moveable axially from said housing end and toward a second and opposite housing end upon said container being removed from said housing.

45. An apparatus for the delivery of an injectable product, comprising:

a housing;

a container received in said housing and including a plunger, an exit and an injectable product between said plunger and said exit;

plunger-engagement means disposed in said housing for drivingly engaging said plunger; and drive means mounted to said housing and axially movable in said housing for moving said plunger-engagement means to drive said plunger within said container, wherein a rotatable piece is secured to said drive stem for rotation therewith, and a locking means is disposed about said drive stem and configured to restrict rotation of said rotatable piece with respect to said housing, said rotatable piece and said locking means biased in unlocked relationship with one another, said rotatable piece and said locking means being forced into locked engagement with one another while said container is mounted to said housing to prevent rotation of said rotatable piece and said plunger-engagement means with respect to said housing, said rotatable piece and said locking means being automatically disengaged from one another upon removal of said container from said housing, thereby permitting said rotatable piece and said plunger-engagement means to be rotated with respect to said housing.

46. A method of delivering a selected dosage of injectable product, the method comprising the steps of:

moving a hand-operated actuator to a pre-injection position;

rotating a knob extending from an injector housing to set a dosage of injectable product to be delivered out of a container mounted to an end of the housing, wherein the injectable product is in the container between a piston and an exit end of the container, wherein movement of the piston toward the exit end defines an axis of ejection of the injectable product from the container; and continuously moving the actuator in a direction transverse to the axis of ejection from the pre-injection position to a post-injection position to move the piston and effect delivery of the injectable product.

47. The method of claim 46, wherein the step of continuously moving the actuator includes moving the actuator through a given angular range of motion, wherein incremental movement of the actuator results in a corresponding incremental axial advancement of a drive assembly which carries a piston-engaging stem.

48. The method of claim 46, wherein the step of rotating includes rotating the knob in a first rotational direction to increase the set dosage and then in a second and opposite rotational direction in order to decrease the set dosage.

49. The method of claim 46, wherein movement of the actuator causes the knob to be rotated back to an initial rotational position.

50. The method of claim 46, wherein the step of moving the actuator to the pre-injection position causes the piston-engaging stem to axially retract off of the piston.

51. A method of delivering a selected dosage of mixed injectable product, the method comprising the steps of:

moving a hand-operated actuator to a pre-injection position;

rotating a first knob of a first dosage metering mechanism disposed in an injector housing to set a first set dosage of first injectable product to be delivered out of a first container mounted in the housing, wherein the first injectable product is in the first container between a first piston and a first exit end of the first container, wherein the first piston is movable toward the first exit end along a first axis of ejection of the first injectable product from the first container;

rotating a second knob of a second dosage metering mechanism disposed in the injector housing to set a second set dosage of second injectable product to be delivered out of a second container mounted in the housing, wherein the second injectable product is in the second container between a second piston and a second exit end of the second container, wherein the second plunger is movable toward the second exit end along a second axis of ejection of the second injectable product from the second container, the second axis being generally parallel to the first axis; and moving the actuator in a direction transverse to the first and second axes of ejection to a post-injection position to simultaneously axially advance first and second piston-engagement members in the housing to axially advance the first and second pistons, respectively, to effect simultaneous delivery of the first and second set dosages into a manifold attached to the first and second exit ends of the first and second containers and out through a needle extending from the manifold.

52. The method of claim 51, wherein the step of moving the actuator includes moving the actuator through a given angular range of motion, wherein incremental movement of the actuator results in a corresponding incremental axial advancement of a drive assembly which carries the first and second members.

53. The method of claim 51, wherein the step of rotating includes rotating at least one of the first and second knobs in a first rotational direction to increase the respective set dosage and then in a second and opposite rotational direction in order to decrease the respective set dosage.

54. The method of claim 51, wherein movement of the actuator causes at least one of the first and second knobs to be rotated back to an initial rotational position.

55. A method of delivering a selected dosage of injectable product, wherein the injectable product is in a cartridge between a piston and an exit end of the cartridge, the cartridge being replaceable and received in a removable cartridge retainer, the cartridge retainer being received in an injector housing and removable to enable the cartridge to be replaced with another cartridge, the method comprising the steps of:

moving a hand-operated mechanism to a pre-injection position, thereby automatically locking the cartridge retainer to the housing;

actuating a dosage metering mechanism disposed in the injector housing to set a dosage of injectable product to be delivered out of the cartridge; and moving the hand-operated mechanism from the pre-injection position to a post-injection position to effect delivery of the injectable product, thereby automatically unlocking the cartridge retainer from the housing to permit the cartridge retainer to be removed from the housing.

56. The method of claim 55, wherein the step of moving the hand-operated mechanism to the pre-injection position automatically prevents the cartridge retainer from being rotatable with respect to the housing, and wherein the step of moving the hand-operated mechanism to the post-injection position automatically permits the cartridge retainer to be rotated with respect to the housing.

57. The method of claim 55, wherein movement of the hand-operated mechanism from the pre-injection position to the post-injection position causes the dosage metering mechanism to be automatically rotated back to an initial rotational position.

58. The method of claim 55, wherein movement of the hand-operated mechanism from the pre-injection position to the post-injection position causes the dosage metering mechanism to be decoupled from a drive mechanism which effects delivery of the injectable product.

59. The method of claim 55, including the step of removing the cartridge retainer and cartridge from the housing while the hand-operated mechanism is in the post-injection position.

60. The method of claim 59, including the step of inserting a second cartridge into the cartridge retainer.

61. The method of claim 60, including the step of attaching the cartridge retainer to the housing while the hand-operated mechanism is in the post-injection position.

62. The method of claim 61, wherein the step of attaching the cartridge retainer to the housing includes the steps of causing a second piston of the second cartridge to engage a piston-engagement member in the injector housing, forcing the piston-engagement member to translate axially within the housing toward the hand-operated member, and rotating the cartridge retainer within the housing to secure the cartridge retainer within the housing.

63. A method of delivering a selected dosage of injectable product, the method comprising the steps of:

rotating a cartridge retainer into a locked position with respect to an injector housing, thereby automatically causing a piston-engagement stem within the housing to become locked against rotation with respect to the housing;

setting a dosage of injectable product to be delivered out of a cartridge of liquid medication housed in the cartridge retainer and containing the liquid medication between a movable piston and an exit;

moving a hand-operated actuator to effect nonrotating axial advancement of the piston-engagement stem to effect delivery of the set dosage of injectable product out of the exit end;

removing the cartridge retainer and cartridge from the housing thereby automatically enabling the piston-engagement stem to be rotatable with respect to the housing; and causing the piston-engagement stem to rotate with respect to the housing and simultaneously axially move toward an opposite end of the housing.

64. The method of claim 63, including the steps of inserting a second cartridge into the cartridge retainer and attaching the cartridge retainer to the housing, thereby automatically causing the piston-engaging stem to axially move toward the opposite end of the housing and then become locked against rotation with respect to the housing upon rotation of the cartridge retainer onto the housing.

* * * * *